(12) United States Patent
Senior et al.

(10) Patent No.: US 10,881,806 B2
(45) Date of Patent: Jan. 5, 2021

(54) DRIVE MECHANISM FOR AN INJECTION DEVICE

(71) Applicant: SANOFI-AVENTIS DEUTSCHLAND GMBH, Frankfurt am Main (DE)

(72) Inventors: James Alexander Senior, Warwick (GB); Elliot Baxter, Warwick (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 281 days.

(21) Appl. No.: 16/061,829

(22) PCT Filed: Dec. 5, 2016

(86) PCT No.: PCT/EP2016/079695
§ 371 (c)(1),
(2) Date: Jun. 13, 2018

(87) PCT Pub. No.: WO2017/102393
PCT Pub. Date: Jun. 22, 2017

(65) Prior Publication Data
US 2018/0361073 A1    Dec. 20, 2018

(30) Foreign Application Priority Data
Dec. 14, 2015    (EP) .................................... 15199709

(51) Int. Cl.
*A61M 5/315*    (2006.01)

(52) U.S. Cl.
CPC .... *A61M 5/31541* (2013.01); *A61M 5/31535* (2013.01); *A61M 5/31543* (2013.01);
(Continued)

(58) Field of Classification Search
CPC ................ A61M 5/20; A61M 5/31525; A61M 5/31528; A61M 5/31533; A61M 5/31535;
(Continued)

(56) References Cited

U.S. PATENT DOCUMENTS

| | | | | |
|---|---|---|---|---|
| 2009/0043264 A1* | 2/2009 | Glejbol | ............. | A61M 5/31585 604/211 |
| 2013/0289518 A1 | 10/2013 | Butler et al. | | |
| 2015/0224266 A1* | 8/2015 | Plumptre | .......... | A61M 5/31593 604/189 |

FOREIGN PATENT DOCUMENTS

| | | |
|---|---|---|
| CN | 101998869 | 3/2011 |
| CN | 105025963 | 11/2015 |

(Continued)

OTHER PUBLICATIONS

PCT International Search Report and Written Opinion in International Appln. No. PCT/EP2016/079695, dated Feb. 20, 2017, 12 pages.

(Continued)

*Primary Examiner* — Brandy S Lee
*Assistant Examiner* — James D Ponton
(74) *Attorney, Agent, or Firm* — Fish & Richardson P.C.

(57) ABSTRACT

A drive mechanism for an injection device for setting and dispensing of a dose of a medicament includes an inner body fixable inside a housing of the injection device, the inner body including an elongated shaft extending in an axial direction. The elongated shaft includes an outer thread and a blocking structure on an outer circumference. The drive mechanism includes a tubular-shaped display member having an inner thread engaged with the outer thread of the inner body, a dose member axially displaceable between a dose setting position and a dose dispensing position relative to the inner body, and a blocking sleeve axially fixed to the dose member, rotationally fixed to the display member and including at least one blocking element to axially engage with the blocking structure to block an axial displacement of the dose member from the dose setting position towards the dose dispensing position.

20 Claims, 12 Drawing Sheets

(52) U.S. Cl.
CPC .... *A61M 5/31551* (2013.01); *A61M 5/31585* (2013.01); *A61M 5/31573* (2013.01); *A61M 5/31575* (2013.01); *A61M 2205/581* (2013.01); *A61M 2205/582* (2013.01)

(58) Field of Classification Search
CPC .......... A61M 5/31541; A61M 5/31543; A61M 5/31545; A61M 5/31548; A61M 5/3155; A61M 5/31551; A61M 5/31553; A61M 5/31556; A61M 5/31585; A61M 5/31575; A61M 5/31573; A61M 2005/2006; A61M 2005/2013; A61M 2005/202; A61M 2005/2026; A61M 2005/2033; A61M 2005/2073

See application file for complete search history.

(56) References Cited

FOREIGN PATENT DOCUMENTS

| | | |
|---|---|---|
| EP | 2292286 | 3/2011 |
| EP | 2404633 | 1/2012 |
| EP | 3256194 | 12/2017 |
| WO | WO 2009/100550 | 8/2009 |
| WO | WO 2012/039139 | 4/2012 |
| WO | WO 2012/049138 | 4/2012 |
| WO | WO 2012/049140 | 4/2012 |
| WO | WO 2014/033195 | 3/2014 |
| WO | WO 2014/033197 | 3/2014 |
| WO | WO 2014/139910 | 9/2014 |
| WO | WO 2014/149909 | 9/2014 |
| WO | WO 2016/128424 | 8/2016 |

OTHER PUBLICATIONS

PCT International Preliminary Report on Patentability in International Appln. No. PCT/EP2016/079695, dated Jun. 19, 2018, 8 pages.

International Search Report and Written Opinion in Application No. PCT/EP2016/079695, dated Feb. 20, 2017, 12 pages.

International Preliminary Report on Patentability in Application No. PCT/EP2016/079695, dated Jun. 19, 2018, 8 pages.

\* cited by examiner

DRIVE MECHANISM FOR AN INJECTION DEVICE

CROSS REFERENCE TO RELATED APPLICATIONS

The present application is the national stage entry of International Patent Application No. PCT/EP2016/079695, filed on Dec. 5, 2016, and claims priority to Application No. EP 15199709.5, filed in on Dec. 14, 2015, the disclosures of which are incorporated herein by reference.

TECHNICAL FIELD

The present disclosure relates in one aspect to a drive mechanism for an injection device, such as a pen-type injector for setting and dispensing of a dose of a medicament. In particular, the disclosure relates to an injection device providing a minimum dose mechanism, i.e. a dose setting and dispensing mechanism that is only operable to dispense a dose if the dose exceeds a predefined minimum threshold.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such as diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, the dose setting as well as dose dispensing procedure must be easy to operate and has to be unambiguous.

Typically, such devices comprise a housing including a particular cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in a distal direction by means of a pierceable seal and being further sealed in proximal direction by the piston. With reusable injection devices an empty cartridge is replaceable by a new one. In contrast, injection devices of disposable type are to be discarded when the medicament in the cartridge has been dispensed or used-up.

Documents WO 2014/033197 A1 and WO 2014/033195 A1 disclose disposable and reusable drug delivery devices for selecting and dispensing a number of user variable doses of a medicament. These devices comprise a housing, a cartridge holder for retaining a cartridge containing the medicament, a piston rod displaceable relative to the cartridge holder, a driver coupled to the piston rod, a display member indicating a set dose and being coupled to a housing and to the driver, and a button coupled to the display member and to the driver.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value but also permits a 'priming' operation to be undertaken before each dose is administered.

A further application could be for a therapy in which a range of discrete, non-sequential pre-defined doses of a medication may be required. For example the range of doses may be needed to satisfy the therapeutic needs of different user groups, or to allow individual users to deliver a different dose at different times of the day e.g. in the morning or in the evening.

SUMMARY

In certain aspects, a drive mechanism for an injection device that provides a minimum dose function is provided. In certain aspects, the drive mechanism also provides a maximum dose function. In certain aspects, a drive mechanism that allows for a priming of the device, so that a user is able to dial and to deliver a rather small volume of medication, typically 2 international units (IU), to check whether flow occurs correctly through a needle assembly releasably attachable to a distal dispensing end of the device.

Implementation of the desired minimum and/or maximum dose function should be achievable by only modifying a limited number of existing device components. It is a further aim to individually modify minimum and maximum dose values or dose sizes by changing only a single component or a few components of the device. Hence, the minimum and/or maximum dose function of the device or its drive mechanism should be configurable by changing only one or a few components of the device or its drive mechanism. It is a further aim, that the improved drive mechanism is universally applicable to a large variety of drive mechanisms and injection devices. In particular, the improved drive mechanism should be equally applicable to disposable injection devices as well as to reusable injection devices. Furthermore, and in one embodiment, the drive mechanism should be operable as a so-called fixed dose mechanism exclusively operable to set and to dispense a single or multiple doses of a pre-defined, hence 'fixed' size.

In a first aspect a drive mechanism for an injection device is featured. The injection device is operable to set and to dispense multiple doses of variable size of a medicament, typically by way of injection. The drive mechanism of the injection device comprises all mechanically inter engaging components that are required to exert distally directed thrust to a piston of a cartridge filled with the liquid medicament. The drive mechanism comprises an inner body that is fixable inside a housing of the injection device. The inner body at least comprises an elongated shaft that extends in an axial direction (z) and having an outer thread. The outer thread is a helical thread and comprises a constant or varying pitch in axial direction. The inner body is fixable inside the housing in a non-movable way. Hence, the inner body is axially as well as rotationally fixable inside a tubular or cylindrically-shaped housing of the injection device. The inner body and the housing may also be integrally formed. Hence, the inner body may consist of a portion of the housing.

The drive mechanism further comprises a tubular-shaped display member having an inner thread engaged or mating with the outer thread of the inner body. The tubular-shaped display member is axially displaceable relative to the inner body, in particular relative to its elongated shaft when rotating in a helical way. Typically, the pitch and friction of the threaded engagement of the display member and the inner body is such that the display member starts to rotate when it is subjected to an axial force effect relative to the inner body.

In addition, the drive mechanism comprises a dose member that is axially displaceable between a dose setting position (S) and a dose dispensing position (D) relative to the inner body. The dose member may be rotatable relative to the inner body. It may be also axially displaceable relative to the inner body. Typically, the dose member is rotatable along a helical path relative to the inner body for setting or dialing of a dose. Moreover, the dose member may be axially displaceable in a non-rotative but purely axial sliding manner relative to the inner body for dispensing of a dose. The dose member and the display member may be selectively rotationally engaged, typically by means of a clutch by way of which the rotational engagement between dose member and display member is either locked or released.

In a dose setting mode the clutch is typically closed, so that a torque applied to the dose member is transferred to the display member, which due to its threaded engagement with the inner body is then displaced axially relative to the inner body in unison with the dose member. For dose dispensing the clutch between display member and dose member may be released or opened so that the display member is allowed to rotate when returning into its initial position while the dose member is subject to a purely translational displacement. Hence, during dose dispensing the dose member may be rotationally locked to the inner body while the display member is free to rotate relative to the display body and hence relative to the dose member.

Depending on the specific embodiment of the drive mechanism either the rotating display member or the translationally displacing dose member is operably engaged with the piston rod for driving the piston rod in a distal dose dispensing direction during dose dispensing for displacing the piston of the cartridge in distal direction.

The dose member and the display member are also axially engaged. When in the dose dispensing position or in the dose dispensing mode, hence when the clutch is disengaged a distally directed displacement of the dose member is transferred to a correspondingly distally directed displacement of the display member. Due to the permanent threaded engagement with the inner body, the display member also rotates and is displaced along a helical path during dose dispensing.

The drive mechanism further comprises a blocking sleeve that is axially fixed to the dose member and which is rotationally fixed to the display member. The blocking sleeve is permanently axially fixed to the dose member. It may be rotatable relative to the dose member. The blocking sleeve is permanently rotationally fixed to the display member. In certain embodiments the blocking sleeve may be slidably displaceable in an axial direction relative to the display member at least to a predefined or limited extent.

The blocking sleeve comprises at least one blocking element to axially engage with the blocking structure to block and to impede an axial displacement of the dose member from the dose setting position towards the dose dispensing position.

The at least one blocking element is rigidly or fixedly attached to the blocking sleeve. It may be an integral component of the blocking sleeve. The blocking sleeve as well as the at least one blocking element are incompressible. The blocking sleeve as well as the at least one blocking element are rather stiff and inelastic. In this way the blocking sleeve and the blocking element may directly engage with the blocking structure. The blocking element and the blocking structure may mutually abut in an axial direction. Typically, a distal edge of the at least one blocking element may engage and axially abut with a proximally facing edge of the blocking structure, thereby blocking a distally directed displacement of the blocking sleeve relative to the blocking structure and hence relative to the inner body. In this way a distally directed displacement of the blocking sleeve and also of the dose member axially fixed thereto can be effectively prevented.

A switching of the drive mechanism from a dose setting mode into a dose dispensing mode by depressing the dose member in distal direction from the dose setting position towards the dose dispensing position is effectively blocked. Hence, as soon as the blocking sleeve with its at least one blocking element engages with the blocking structure on the outer circumference of the inner body the drive mechanism and hence the entire drug delivery device cannot be switched into a dose dispensing mode. Dose dispensing is therefore blocked and impeded.

In one embodiment the at least one blocking element is integrally formed with the blocking sleeve. The blocking sleeve as well as the majority of the other components of the drive mechanism is configured as an injection molded plastic part. In this way even a rather complex geometric structure of the blocking sleeve and of all the further components can be manufactured with high precision at moderate costs and in large quantities.

The drive mechanism is configured such that application of distally directed thrust to the dose member leads to a distally directed displacement thereof only when the clutch between the dose member and the display member is released so that a display member is free to rotate relative to the dose member. During dose dispensing the dose member is rotationally fixed relative to the inner body and hence to the housing. It is purely axially displaceable relative to the inner body and hence to the housing during a dose dispensing procedure. In order to release and to disengage a torque transferring clutch between the dose member and the display member a small but distinct axial displacement of the dose member relative to the display member is required. As long as the blocking element is engaged with the blocking structure and axially abuts with the blocking structure an axial displacement of the dose member relative to the display member to such a degree that the clutch therebetween would release is effectively prevented. As long as the blocking element is in axial engagement or abutment with the blocking structure a distally directed displacement of the dose member relative to the display member is effectively impeded and the clutch between the dose member and the display member is prevented from disengaging.

Depending on the geometric design and extension of the blocking structure, dose dispensing can be effectively blocked for a predefined range of dose sizes. In this way, minimum and maximum thresholds can be defined between which dose dispensing is effectively blocked and prevented.

A minimum threshold may define a maximum dose value for a priming procedure, e.g. 2 or 3 IU. A maximum threshold could define a minimum dose size, hence a dose size that has at least to be dispensed by the drive mechanism in order to ensure sufficient delivery of e.g. one element of a combined drug to obtain a desired therapeutic effect.

The geometric design of the blocking structure may also define only single dose values that may be dispensable with the drive mechanism and with the injection device. Alternatively, the mutual interaction between the blocking structure and the dose member may be configured such that only particular sequential or non-sequential set of dose values are dispensable. It is conceivable, that the drive mechanism only allows setting and subsequent dispensing of a sequential range of doses, such as 10 IU, 11 IU, 12 IU or a non-sequential range of doses, such like 10 IU, 13 IU, 23 IU, etc. Such functionality may be of particular use for administering a combination of liquid medicaments, where injection of a minimum quantity of combined medicaments is required to ensure sufficient delivery of one element of a combination to be therapeutically effective, whilst allowing some variation of the dose, which may be important for the other element of the respective combination.

For some applications it may be of particular benefit to offer an injection device that allows delivery of only one fixed dose value but that also permits a 'priming' operation to be undertaken before each dose is administered. The device and its drive mechanism may be of further use for such therapies in which a range of discrete, non-sequential doses of a medicament may be required. For example a range of doses may be needed to satisfy therapeutic needs of different user groups or to allow individual users to deliver a different dose at different times of the day, e.g. morning and evening.

All these different demands can be easily fulfilled by the specific shape, design and geometry of the blocking structure on the outer cylindrical surface of the inner body. A general behavior of the drive mechanism and hence of the respective injection device may be individually switched and adapted to different requirements simply by exchanging only the inner body whilst leaving all other components of the drive mechanism unchanged. This is of particular benefit from a manufacturer's point of view. By means of modifying only one of a plurality of components of a drive mechanism the general functionality and dispensing behavior of the drive mechanism can be changed.

Therefore, and according to one embodiment the drive mechanism comprises a torque transferring clutch between the dose member and the display member, wherein the clutch is closed when the dose member is in the dose setting position and wherein the clutch is disengageable by an axial displacement of the dose member relative to the display member. In a further embodiment a distally directed displacement of the dose member relative to the display member is effectively impeded as long as the blocking element is in axial engagement or axial abutment with the blocking structure.

According to another embodiment the blocking structure comprises a blocking thread on the elongated shaft. It is located on the outer circumference of the elongated shaft. The blocking thread may extend between convolutions of the outer thread of the inner body. In further embodiments the blocking thread is located axially offset from the outer thread of the shaft. It may be axially separated from the outer thread of the shaft. The blocking structure or blocking thread may be located at a proximal section of the elongated shaft while the outer thread may be located at a distal section of the outer shaft. The blocking thread and the outer thread may be axially non-overlapping and may be axially separated by a predefined non-zero distance. The blocking thread and the outer thread have the same pitch. Since the blocking thread and the outer thread have the same pitch and since the blocking thread and the outer thread are axially offset the blocking element remains in its blocking position during engagement with the blocking thread when the display member is subject to a helical rotation relative to the inner body during a dose dialing operation. The radial extension of the blocking structure and hence of the blocking thread may be substantially equal to the radial extension of the outer thread.

Since the blocking structure and the outer thread have the same pitch a rotation of the dose member relative to the housing and hence relative to the inner body for setting or dialing of a dose will be always possible. As long as the dose member is in a dose setting position the geometry and design of the at least one blocking element and the blocking structure is such that the blocking element may pass along or slide along the blocking structure in accordance to the helical motion of the dose member relative to the inner body. While in the dose setting position and when dialing or setting a dose of a particular size the at least one blocking element is located proximally from a proximal edge of the blocking structure. The at least one blocking element may even gently touch or gently slide along a proximal edge of the blocking structure as long as the dose member is in its dose setting position.

A distally directed displacement of the dose member relative to the display member for switching from the dose setting position towards the dose dispensing position then leads to an axial engagement of the at least one blocking element with the blocking structure. The at least one blocking element and the blocking thread substantially overlap in the radial and tangential direction as seen in an axial projection. Hence, the at least one blocking element enters the free space between two consecutive convolutions of the blocking thread as the blocking sleeve and the display member are rotated or dialed for setting of a dose. Due to the axial abutment between the at least one blocking element and the blocking thread a distally directed displacement of the dose member is impeded.

Since the blocking thread and the outer thread have the same pitch the blocking functionality provided by the blocking element and the blocking structure is idle as long as the dose member is rotated relative to the inner body in accordance with the threaded engagement of inner body and display member.

According to another embodiment the blocking structure comprises at least one spiral-shaped blocking segment and at least one gap or edge having a tangential size larger than or equal to a tangential size of the blocking element. The gap is located in the blocking segment and may interrupt the blocking segment, thereby splitting the at least one spiral shaped blocking segment into two blocking segments. Then the two spiral-shaped blocking segments separated in a tangential direction by the at least one gap. The at least one gap has a tangential width or size that is larger than or equal to the tangential width or size of the blocking element. In other words, the at least one gap intersects the blocking thread. The blocking thread may even be constituted by several or by a multitude of blocking segments. In other words, the blocking segments are only portions or segments of the blocking thread that are separated by defined gaps. The position and size of the gaps define the dose sizes or a range of dose sizes for which the drive mechanism is switchable from a dose setting position into a dose dispensing position.

The gap of appropriate size may by also located at an axial end of the spiral-shaped blocking structure. Then the gap is basically formed by an edge of the blocking structure.

The position and size of the gaps therefore define those doses and dose ranges for which application and administering of the medicament is supported and allowable. Since the tangential or circumferential size of the at least one gap is larger than or equal to the tangential size of the at least one blocking element, the blocking element is able to pass through the respective gap only if the dose member is in a helical position that corresponds to a supported and allowable dose size. In such a configuration the at least one blocking element is axially aligned with or overlaps with the at least one gap but is located proximally from the blocking segment that is located tangentially adjacent to said gap. Due to the fact that a tangential size or extension of the at least one blocking element is smaller than or equal to the tangential or circumferential size of the at least one gap a smooth axial and distally directed displacement of the dose member relative to the inner body is supported and allowed.

Consequently, the dose member is then displaceable in the distal direction to such a degree that the clutch between the dose member and the display member is opened and released. The drive mechanism is then switched into the dispensing mode in which the dose member is purely axially and distally displaceable and in which the rotational coupling between the dose member and the display member is suspended thus allowing the display member to rotate in a dose decrementing direction, hence in a direction of rotation opposite to a dose incrementing dialing motion for setting of a dose. With the clutch disengaged or released the dose member and the display member may still be at least coupled in axial direction. A distally directed displacement or sliding motion of the dose member is then transferred to the display member, which due to a permanent threaded engagement with the inner body, starts to rotate in the dose decrementing direction.

According to a further embodiment the blocking sleeve at least partially encloses the inner body and the at least one blocking element protrudes radially inwardly from a sidewall of the blocking sleeve. The radially inwardly directed extension of the at least one blocking element substantially coincides or corresponds with the radial dimensions of the blocking structure. The radial size of the at least one blocking element is as large so as to enter the free space between the convolutions of the helical blocking thread. In this way an effective blocking of a distally directed displacement of the blocking sleeve and hence of the dose member can be impeded as long as the blocking element overlaps in a tangential and radial direction with a blocking segment of the blocking structure as seen in an axial projection. Only when the at least one blocking element fully coincides with a gap of the blocking structure a distally directed displacement of the blocking sleeve and hence of the dose member relative to the inner body and relative to the display member or relative to a part of the display member that is threadedly engaged with the inner body is allowed and supported, thereby disengaging the clutch between the dose member and the display member.

It is further conceivable that the blocking sleeve comprises several blocking elements formed on the inside of the blocking sleeve. A multitude of blocking elements can be arranged in a common lateral plane perpendicular to the longitudinal extension of the blocking sleeve. In other embodiments various blocking elements may be arranged axially offset. In particular embodiments there are provided at least three or four blocking elements on the inside of the blocking sleeve. Typically, the blocking elements are equidistantly separated around the inner circumference of the blocking sleeve. Accordingly, the blocking structure may comprise not only one but several blocking threads that are nested relative to each other.

It is conceivable, that all blocking threads of a plurality of blocking threads are identical but that the blocking threads are circumferentially offset in accordance with a circumferential offset of the respective blocking elements of the blocking sleeve. In this way numerous blocking elements may simultaneously engage with numerous blocking threads when the drive mechanism is in a blocking configuration. When in a release configuration, in which dispensing of a dose is allowed and supported all blocking elements are aligned and overlap with respective gaps of the blocking thread. By having a plurality of blocking elements on the sidewall of the blocking sleeve an axial load applied to the blocking sleeve is homogeneously transferable into the blocking structure and hence into the blocking thread and into its various blocking segments. In this way, the axial load to be transferred by the blocking sleeve can be somewhat homogeneously transferred to the inner body and can be hence homogeneously counteracted by the inner body.

The total axial load present to the dose member and hence to the blocking sleeve may be distributed among the various blocking elements that are simultaneously engaged with respective blocking segments of the blocking structure. The mechanical or axial load acting on each one of the blocking elements can therefore be reduced. Hence, the blocking elements will be less prone to damage or fracture if a mechanical load above a certain threshold should be applied to the dose member or to the blocking sleeve.

According to another embodiment the at least one blocking element extends radially inwardly through an aperture in a sidewall of the display member. In this way the blocking sleeve also encloses at least a portion of the display member or a part thereof. By reaching through the aperture of the display member the blocking sleeve can be arranged on the outer circumference of the display member. In this way a nested arrangement of the blocking sleeve and the display member is provided and the blocking sleeve is enabled to directly engage with the blocking structure on the outer circumference of the inner body.

By means of the at least one blocking element extending through the sidewall of the display member a rotational engagement and rotational fixing of the blocking sleeve and the display member can be obtained. Here, the circumferential width of the aperture in the sidewall of the display member closely matches the circumferential or tangential width of the at least one blocking element. Then the blocking sleeve and the display member are permanently rotationally locked by means of the blocking element or by means of several blocking elements. By means of the at least one blocking element and the correspondingly-shaped aperture a positive rotational engagement between the blocking sleeve and the display member can be obtained.

The at least one blocking element and the at least one correspondingly-shaped aperture may provide a snap-fit engagement of the blocking sleeve and the display member. If the blocking sleeve is provided with several blocking elements, the display member comprises a respective number of apertures in its sidewall to receive the respective blocking elements. This leads to a slack-free and rather rigid rotational connection between the blocking sleeve and the display member. The at least one blocking element therefore has a double function. It provides axial engagement between the blocking sleeve and the blocking structure with limited permissible axial travel and it provides a rotational engagement between the blocking sleeve and the display member.

The at least one aperture of the display member typically comprises an axial elongation that is substantially larger than the respective axial length or axial extension of the correspondingly-shaped blocking element of the blocking sleeve. In this way an axial sliding displacement between the blocking sleeve and the display member is provided. In situations where the at least one blocking element aligns with a gap of the blocking structure the blocking sleeve is then axially displaceable relative to the display member in order to disengage and to release the clutch between the dose member and the display member or between a driver of the drive mechanism and the display member.

In another embodiment the blocking sleeve encloses at least an axial section of the display member or a part of the display member. In this way the blocking sleeve may be axially guided by the display member located radially inside the blocking sleeve. In other words, by enclosing at least an axial section of the display member the blocking sleeve can be rotationally guided by the display member.

In another embodiment the dose member comprises a dose button. The dose button may also serve as a dose dial and may be hence also denoted as dose dial. In one embodiment it comprises a button part and a dial part. The button part forms a proximal and planar end face of the dose member. For dispensing of a dose a user typically depresses the dose button in distal direction, e.g. by making use of his thumb. The dial part is positively attachable and fixable to the button part and includes an annular groove to axially engage with a proximal end section of the blocking sleeve.

When the button part and the dial part are mutually attached and fixed relative to each other the button part and the dial part are also rotationally engaged. The dial part may comprise a somewhat tubular shape and may form an outer rim of the dose button. Once mutually attached and fixed the dial part is rotatable, thereby also rotating the button part. It is typically the button part that is further provided with a longitudinally or axially extending cylindrical portion. By means of the cylindrical portion the dose member may be either rigidly attached to a clutch sleeve that is selectively rotatable and rotationally lockable to the inner body or to the housing of the injection device.

When mutually attached and fixed the button part and the dial part form and annular groove that is configured to receive a proximal end section of the blocking sleeve. The proximal end section of the blocking sleeve may comprise one or several snap elements that may be clipped into the annular groove. The axial width of the annular groove substantially matches the axial length of a fastening element at the proximal end section of the blocking sleeve. The fastening element may comprise a locking tab that can be rigidly fastened in the annular groove of the dose member. In this way the dose member is axially fastened and axially fixed to the blocking sleeve whilst also being free to rotate relative to the blocking sleeve.

The annular groove is constituted by both, the button part and the dial part. It provides a rather stable and strong axial connection of the dose member to the display member. This type of fastening is beneficial in that it withstands attempts to disconnect the dose member and the blocking sleeve, in the event that a user erroneously applies a rather large force effect to the dose member in proximal direction. Providing of the annular groove between the dial part and the button part also provides a rather frictionless rotational fit between the dose member and the blocking sleeve. Since the blocking sleeve rotates during dose dispensing while the dose member is rotationally fixed a free-running rotational fit therebetween reduces the resultant dispensing force that has to be applied by a user to conduct a dispensing procedure.

Typically, in a dose setting position, the dose member is rotatable relative to the inner body or relative to the housing of the injection device under the action of a clicker producing clicking noises every time the dose member is rotated by a discrete angular distance. In the dose dispensing position, in which the dose member is depressed in a distal direction the dose member is typically rotationally locked to the housing of the injection device via the clicker and by an axial and rotational engagement of a clutch sleeve with the clicker.

In another embodiment the display member comprises a dial sleeve and a number sleeve that are rotationally fixed to each other. One of the dial sleeve or number sleeve is threadedly engaged with the inner body and the other one of the dial sleeve or number sleeve forms the blocking sleeve and is engageable with the blocking structure. In this embodiment the blocking sleeve coincides with one part of the display member, either with the dial sleeve or with the number sleeve. The number sleeve comprises a sequence of dose indicating numbers on its outer circumference that show up in an aperture or in a window of the housing of the injection device.

In one embodiment the dial sleeve is rotationally fixed to the number sleeve but is axially displaceable relative to the number sleeve. In this way the dial sleeve and the number sleeve are axially displaceable to a certain degree that is sufficient to disengage the clutch between the display member and the dose member for the purpose of dose dispensing. The dial sleeve is typically that component of the display member that is selectively rotationally engageable with the dose member. It is typically the dial sleeve that comprises a toothed structure at an outer or inner circumference near a proximal end so as to engage with a correspondingly-shaped toothed structure of the clutch sleeve rigidly fastened to the dose member or with a correspondingly-shaped toothed structure of a driver that is rotationally engageable but slidably displaceable relative to the dose member.

By arranging the at least one blocking element on one of the number sleeve or dial sleeve the total number of parts of the drive mechanism can be effectively reduced. So if one of the components of the display member, the dial sleeve or the number sleeve effectively acts as the blocking sleeve as described above a separate blocking sleeve is not required. This requires however a slight relative axial displacement between the dial sleeve and the number sleeve.

In various embodiments the dial sleeve and the number sleeve effectively co-align in axial direction. So the dial sleeve may be configured and designed as a longitudinal extension of the number sleeve. With a separate blocking sleeve the dial sleeve and the number sleeve might be rigidly fixed to each other, e.g. by a snap-fit connection. In other embodiments the dial sleeve and the number sleeve may be arranged in an at least partially axially overlapping or nested manner. It is conceivable, that an innermost sleeve component comprises the inner thread and is further threadedly engaged with the outer thread of the inner body.

The outer component enclosing the inner component is then typically provided with the at least one radially inwardly extending blocking element. If the at least one blocking element axially overlaps with the inner component of the display member it may directly engage with the blocking structure. If the at least one blocking element is located at an axial position on the outer component that axially overlaps with the inner component the inner component typically comprises an aperture in a sidewall or a recess in a sidewall through which the at least one blocking element may extend. Depending on the specific embodiment one of the dial sleeve and the number sleeve is the inner component of the display member and the other one of dial sleeve and number sleeve is the outer component of the display member.

According to a further embodiment the blocking structure is located at a distal section or at a distal end section of the inner body. The at least one blocking element then protrudes radially inwardly from a sidewall of the number sleeve. The at least one blocking element and the inner thread are typically separated by an axial distance that is typically larger than the axial extension of the blocking structure or of the inner thread. This is of particular benefit when the outer thread and the blocking structure of the inner body are arranged in a non-overlapping way and when the outer thread and the blocking structure are axially separated.

With the at least one blocking element located on the number sleeve the number sleeve is actually subject to a gentle and rather short distally directed displacement relative to the inner body as the drive mechanism is switched from the dose setting mode into the dose dispensing mode. Generally, the dial sleeve is located at or forms a proximal end of the display member and the number sleeve is located at or forms a distal end of the display member.

According to a further embodiment the outer thread is located at a proximal section of the inner body and the inner thread is located on the dial sleeve. Logically, the inner thread is threadedly engaged with the outer thread. It is hence the dial sleeve that is threadedly engaged with the inner body and which is displaceable in axial direction relative to the inner body only by way of a helical motion in accordance with the pitch of the outer thread. The inner thread may be configured as a threaded section. It may be smaller or shorter than one revolution of the inner threaded structure. The inner thread may be just spiral-shaped with a pitch that corresponds to the pitch of the outer thread of the inner body.

In this embodiment the dial sleeve encloses a major portion of the dial sleeve. The number sleeve and the dial sleeve are rotationally locked, e.g. by means of a radially protruding and axially elongated structure on one of the dial sleeve and number sleeve received in a correspondingly-shaped recess or through opening of the other one of the dial sleeve and number sleeve. In this embodiment it is typically the number sleeve that is axially engaged with the dose member at its proximal end. However and in order to selectively engage with a clutch the dial sleeve may extend from the proximal end of the number sleeve. In this way a clicker feature attached to or located on the outer circumference of the dial sleeve may engage with a correspondingly-shaped toothed structure on the inside of the dose member, thereby generating an audible noise and hence an audible feedback to the user during dose dispensing.

According to a further embodiment the drive mechanism comprises a piston rod and a tubular-shaped driver, both extending in the axial direction. The piston rod typically comprises a first outer thread engaged with an inner thread of the inner body. In this way, a rotation of the piston rod in a dispensing direction leads to a distally directed advancing of the piston rod relative to the inner body and hence relative to the cartridge, which is axially constrained inside the housing of the injection device. The piston rod may further comprise a second outer thread of opposite hand compared to the first outer thread, wherein the second outer thread is threadedly engaged with an inner thread of the driver. In this way, an axial but non-rotative displacement of the driver in the distal direction induces a rotation of the piston rod which due to the threaded engagement with the inner thread of the inner body advances it in the distal direction during dose dispensing. Hence, during dose dispensing the driver is subject to a distally directed purely translational but non-rotational movement. For dose dispensing the driver is rotationally locked to the inner body. It may be coupled to splines in the inner body so that the driver is prevented from rotating relative to the body but is free to be axially displaced relative to the body during dose dispensing.

In a dose setting configuration the driver may be rotationally locked or coupled to the display member so as to follow the helical motion of the display member relative to the inner body. In dose setting mode, a splined engagement of driver and inner body is abrogated or released. Instead, the driver is free to rotate in accordance to a helical path that coincides with the threaded engagement of driver and piston rod so that the driver is axially displaceable in proximal direction relative to the inner body and relative to the piston rod, which during dose setting is stationary with regard to the inner body.

By means of the two threads of the piston rod of opposite hand a displacement transition ratio between the distally directed displacement of the driver and the piston rod can be implemented. A rather large axial displacement requiring a rather low dispensing force can therefore be transferred into a rather short displacement of the piston rod with a rather large dispensing force.

According to another embodiment the dose member is permanently rotationally locked to the driver. The driver in turn is selectively rotationally lockable to the inner body by displacing the dose member into the dose dispensing position. When the dose member is in the dose setting position the driver is no longer rotationally locked to the body but is free to rotate relative to the body, e.g. by means of a clicker detent engagement by way of which the rotation of the driver relative to the body produces an audible and tactile click sound thereby indicating to the user, that subsequent discrete steps of dose setting actually take place.

The driver and the display member may be axially engaged either directly or indirectly via an axial engagement of the dose member with both the driver and the display member.

When implemented as a mechanism for a disposable injection device the dose member and the driver may be permanently rotationally locked. For instance, the dose member and driver may be splined together so that the dose member is prevented from rotating during dose dispensing by the driver being rotationally locked to the inner body.

According to another embodiment the driver is rotationally locked to the dose member and the driver is further rotationally engageable with the display member by means of a clutch. Typically, the driver is directly rotationally engageable with the display member by means of the clutch. The clutch is operable to:
  rotationally engage the driver and the display member when the dose member is in the dose setting position and further
  to rotationally release the display member from the driver when the dose member is in the dose dispensing position.

A rotational engagement means a torque transferring engagement between the respective components. With this embodiment the driver is permanently rotationally locked to the dose member and the dose member is selectively rotationally engageable with the display member via the clutch, hence via the driver. So the display member is axially displaceable relative to the driver for switching the drive mechanism from a dose setting mode into a dose dispensing mode. Here, the driver, typically a proximal end thereof, comprises a toothed structure to selectively engage with a correspondingly toothed structure of the display member. Axial displacement of the display member, typically in a distal direction relative to the driver then disengages the mutually corresponding toothed structures, thereby releasing and allowing a rotation of the display member relative to the driver. As the dose member is depressed in a distal direction it may axially engage with the driver so that the driver is actually prevented to move in proximal direction. This may rotationally lock the driver to the inner body since it has to stay in rotational engagement with a clicker that is axially displaceable only in proximal direction but which is rotationally fixed inside the inner body.

This embodiment is of particular advantage because a separate blocking sleeve is not required. Here, the display member, in particular a dial sleeve thereof effectively acts as the blocking sleeve having at least one radially inwardly extending blocking element rigidly attached thereto. This embodiment is of particular advantage in that the dial sleeve but not the number sleeve is subject to axial displacement when switching the drive mechanism from the dose setting mode into the dose dispensing mode. Consequently, the number sleeve and the numbers shown in a display of the drive mechanism are axially fixed while the drive mechanism is switched between the dose setting mode and the dose dispensing mode.

In another embodiment the dose member is axially fixed to the display member. The dose member itself may be freely rotatable relative to the display member. During dose setting the dose member is rotationally fixed with regard to the display member and hence with regard to the dial sleeve via the driver and the torque transferring clutch acting between the display member and the driver.

In another embodiment the dose member is axially displaceable relative to the driver in an axial distal direction against the action of a spring. The spring is axially sandwiched between the dose member and the driver. So the dose member is axially displaceable in distal direction against the action of the spring. For supporting the spring the driver may comprise a radial recess or protrusion to receive the spring and the dose member or at least a radially stepped portion of an elongated stem or dose sleeve portion thereof engages with an opposite end of the spring.

In another aspect an injection device for setting and dispensing of a dose of a medicament is featured. The injection device is typically configured as a pen-type injector. It comprises an elongated housing to accommodate a drive mechanism as described above and a cartridge arranged inside the housing and filled with a liquid medicament. The cartridge is typically located within and accommodated by a cartridge holder forming a distal portion of the housing of the injection device. When the injection device is implemented as a disposable device the cartridge holder and the proximal housing component are typically permanently interconnected. This connection is of non-disconnectable type. Separation of the proximal housing and the cartridge holder requires destruction or breaking of one of these components. When implemented as a reusable device the cartridge holder is releasably connected with the proximal housing part so as to provide access to the cartridge for cartridge replacement as well as to enable a reset operation of the drive mechanism.

In the present context, the distal direction points in the direction of the dispensing end of the device, where, preferably a needle assembly is provided having a double-tipped injection needle that is to be inserted into biological tissue or into the skin of a patient for delivery of the medicament.

The proximal end or proximal direction denotes the end of the device or a component thereof, which is furthest away from the dispensing end. Typically, an actuating member or dose member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a proteine, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp- Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:
H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39),
wherein the group -Lys6-NH2 may be bound to the C-terminus of the Exendin-4 derivative;
or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-desPro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2,
H-(Lys)6-des Pro36, Pro37, Pro38 [Met(O)14, Asp28] Exendin-4(1-39)-(Lys)6-NH2,
H-Asn-(Glu)5 des Pro36, Pro37, Pro38 [Met(O)14, Asp28] Exendin-4(1-39)-(Lys)6-NH2,
H-Lys6-des Pro36 [Met(O)14, Trp(O2)25, Asp28] Exendin-4(1-39)-Lys6-NH2,
H-des Asp28 Pro36, Pro37, Pro38 [Met(O)14, Trp(O2)25] Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Trp(O2)25, Asp28] Exendin-4(1-39)-NH2,
des Pro36, Pro37, Pro38 [Met(O)14, Trp(O2)25, Asp28] Exendin-4(1-39)-(Lys)6-NH2,
H-(Lys)6-des Pro36, Pro37, Pro38 [Met(O)14, Trp(O2)25, Asp28] Exendin-4(S1-39)-(Lys)6-NH2,
H-Asn-(Glu)5-des Pro36, Pro37, Pro38 [Met(O)14, Trp(O2)25, Asp28] Exendin-4(1-39)-(Lys)6-NH2;
or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE FIGURES

In the following, embodiments of the drive mechanism and the injection device are described in detail by making reference to the drawings, in which.

DETAILED DESCRIPTION

Figure 1:
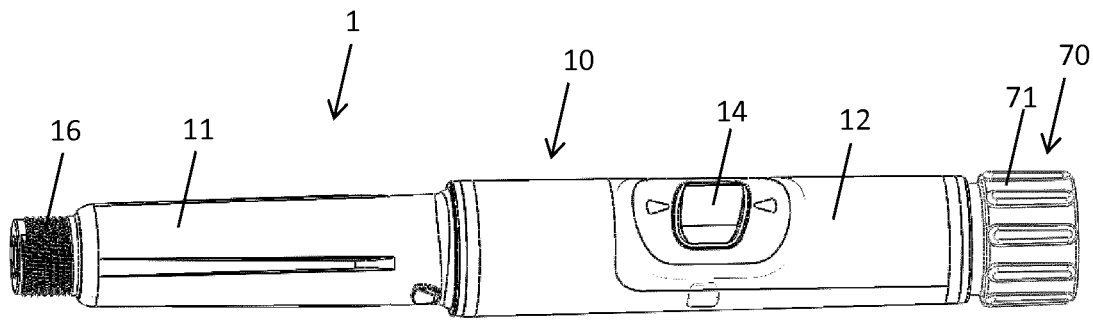
FIG. 1 shows a perspective outer view of the injection device.
Figure 2:
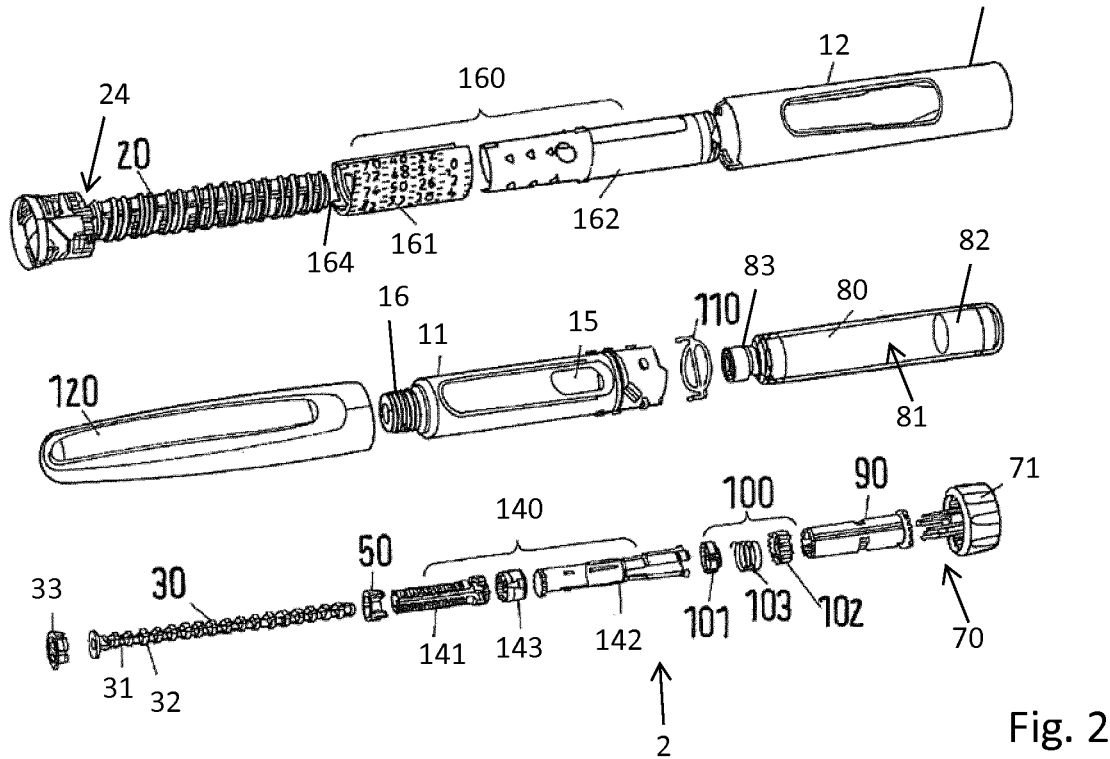
FIG. 2 shows an exploded view of an embodiment of the injection device.
Figure 3:
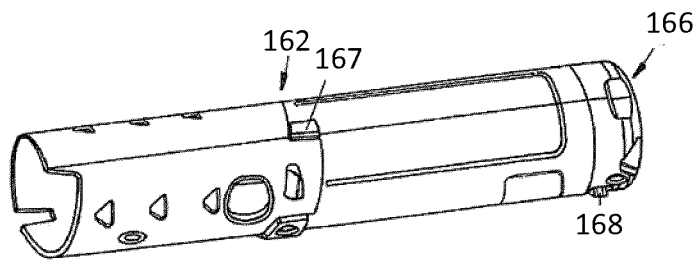
FIG. 3 shows a dial sleeve of the display member according to FIG. 2.

FIG. 1 shows a drug delivery device 1 in the form of an injection pen. The device has a distal end, shown as left end in FIG. 1 and a proximal end located at the right hand side FIG. 1. The components or parts of the drug delivery device 1 and its drive mechanism 2 are shown in FIG. 2 in more detail but without showing the blocking sleeve 172 with blocking elements 174 and without showing the blocking structure 40. The drug delivery device 1 comprises an outer housing part 12, a cartridge holder 11, an inner body 20, a piston rod 30, a driver 140, a last dose nut 50, a display member 160, a dose member 70, a cartridge 80 and a cap 120. Even though not shown in FIG. 2, a needle arrangement comprising a needle hub and a needle cover may be provided as additional components, which can be exchanged. The general concept and structure of the drive mechanism as shown in FIGS. 2 to 18 is similar and partially identical to a re-usable mechanism disclosed in WO 2014/033195 A1, which is incorporated herein by reference. The drive mechanism may be also implemented as a disposable drive mechanism being void of a reset function as disclosed in WO 2014/033197 A1, which is also incorporated herein by reference.

The cartridge 80 includes a pre-filled, necked-down cartridge reservoir 81, which may be typically made of glass. A rubber type bung 82 or stopper is located at the proximal end of the cartridge reservoir 81, and a pierceable rubber seal (not shown) is located at the other, distal, end. A crimped annular metal cap 83 is used to hold the rubber seal in place. The cartridge 80 is provided within the cartridge holder 11 with bearing 33 of piston rod 30 abutting bung 82. FIG. 2 shows the cap 120 which is detachable from the distal end of the device 1, thus giving access to the cartridge holder 11. The cap 120 may be releasably snapped onto the outer housing 10 and can be taken off for use of the device 1.

The outer housing part 12 is a generally tubular element forming a proximal part of the housing 10 of the device 1. A cartridge holder 11 for receiving the cartridge 80 and forming a distal part of the housing 10 is detachably connectable to the proximal housing part 12, which forms an outer body. In one embodiment, the outer housing is transparent, with the outer body 12 being provided with an opaque layer 13. In FIG. 1, the opaque layer 13 covers most of the outer body 12 with the exception of a transparent window 14. Apertures 15 may be provided in the cartridge holder 11. Further, at its distal end the cartridge holder 11 has a thread 16 or the like for attaching the needle hub 2.

The inner body 20 is a generally tubular element having different diameter regions. The inner body 20 is received in the outer body 12 and permanently fixed therein to prevent any relative movement of the inner body 20 with respect to the outer body 12. An external thread 21 is provided on the outer surface of a shaft portion 20a of the inner body 20. Further, splines 22 are provided on the inner surface of the inner body 206 The inner body 20 has near its distal end an inner thread 23.

The piston rod 30 is an elongated element having two external threads 31, 32 with opposite hand which overlap each other. One of these threads 31 engages the inner thread 23 of the inner body 20. A disk-like bearing 33 is provided at the distal end of the piston rod 30. The bearing 33 may be attached to the piston rod 30 as a one-piece component via a predetermined breaking point. This allows that the bearing 33 is separated from the piston rod 30 such that the bearing 33 remains seated on the distal end of the piston rod 30 to allow relative rotation between the bearing 33 and the piston rod 30.

In this embodiment, the driver 140 is a generally tubular element having in the embodiment shown in the Figures three components 141, 142, 143 which are depicted in FIGS. 2, 5, 6 and 8 in more detail. The driver 140 comprises a distal drive sleeve 141, a proximal drive sleeve 142 and a coupler 143. The distal drive sleeve 141 engages with the piston rod thread 32 to drive the piston rod 30 through the inner body 20 during dose delivery. An inner thread 142a of the distal drive sleeve 141 is threadedly engaged with the piston rod thread 32. The distal drive sleeve 141 is also permanently connected to the coupler 143 which in turn is releasably engaged through reset clutch features to the proximal drive sleeve 142. The two halves of the drive sleeve 141, 142 are rotationally and axially connected during dialing and dispense, but are decoupled rotationally during device reset so that they can rotate relative to each other.

Figure 8:
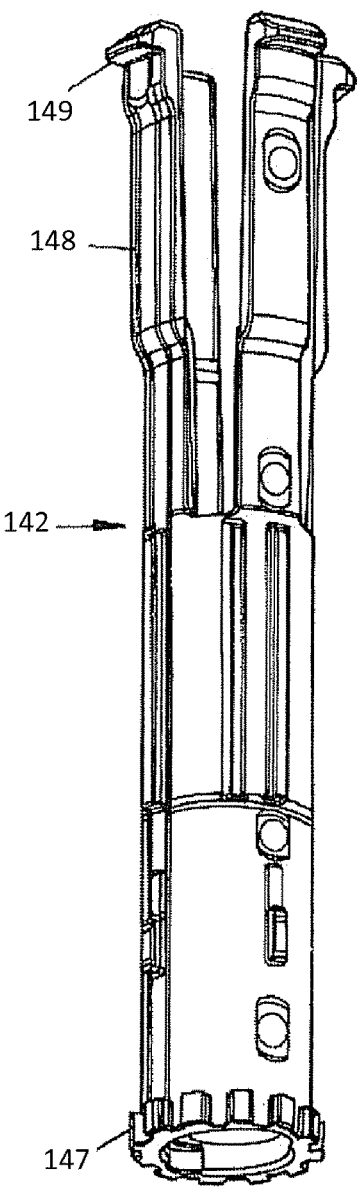
FIG. 8 shows a proximal driver part.
Figure 9:
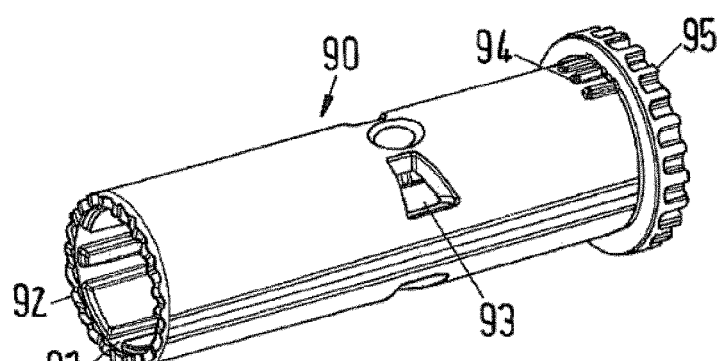
FIG. 9 shows a clutch sleeve.
Figure 10:
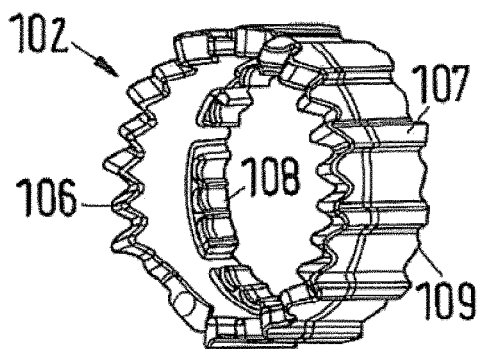
FIG. 10 is an isolated view of a proximal clicker part.
Figure 11:
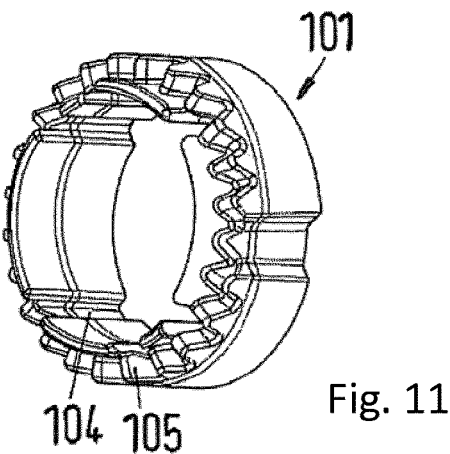
FIG. 11 is an isolated view of a distal clicker part.
Figure 12:
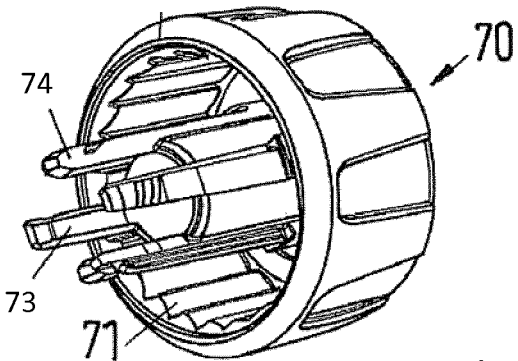
FIG. 12 shows a proximal part of the dose member.
Figure 13:
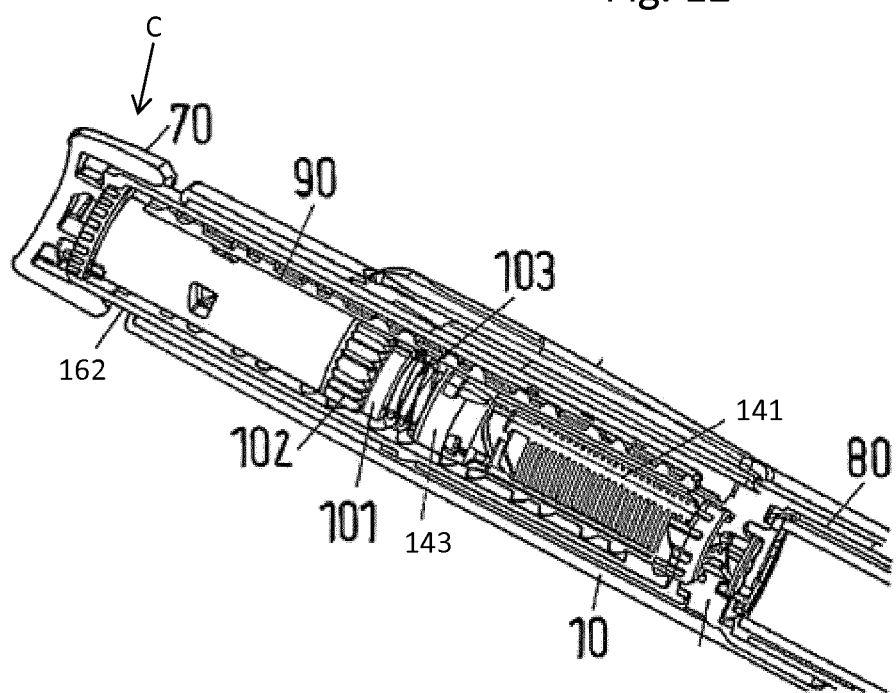
FIG. 13 is a partially cut view through the drive mechanism when assembled in the injection device.

The proximal drive sleeve 142 shown in FIG. 8 supports components of a clicker 100 and sleeve shaped clutch sleeve 90 and transfers rotational movement from the dose member 70 to the coupler 143 and distal drive sleeve 141. Teeth features 147 located at the distal end of proximal drive sleeve 142 engage with the reset clutch features on the coupler 143 to connect both halves of the drive sleeve during dialing and dispense. During reset these teeth 147 disengage.

Several splines are provided on the outer surface of proximal drive sleeve 142 engaging with a distal clicker part 101, preventing relative rotation during dialing and dispense. Further splines, which are located in the middle region of proximal drive sleeve 142, engage with the clutch sleeve 90 component. They may be arranged to be non-rotationally symmetric so that the various clicker components cannot be assembled accidentally upside down.

The proximal portion of proximal drive sleeve 142 has four arms or fingers 148. A hook-like bearing surface 149 exists on the underside of flange segments on the end of the flexible fingers 148 as seen in FIG. 8. The flexible fingers 148 are separated with gaps or slots that make space for the dose member 70 to snap to the clutch sleeve 90 and also enable these fingers to flex inwards during assembly of the proximal drive sleeve 142 to a dial sleeve 162. After assembly the hooks 149 retain the proximal drive sleeve 142 relative to the dial sleeve 162 under the reaction force from the spring 103.

During dispense the dose member 70 depresses the spring 103 via the clutch sleeve 90 and the clicker components and this spring 103 is reacted through the coupler 143 to the proximal drive sleeve 142 which then through bearing surfaces 149 applies axial load to the dial sleeve 162. This axial load drives the dial sleeve 162 and hence a number sleeve 161 along the helical thread of the inner body 20, back into the body of the device, until the zero dose stop faces 164 on the number sleeve 161 contact the inner body 20.

Figure 6:
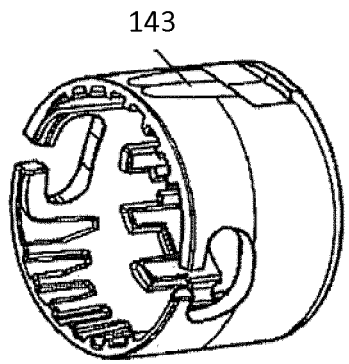
FIG. 6 shows an isolated view of a coupler.
Figure 7:
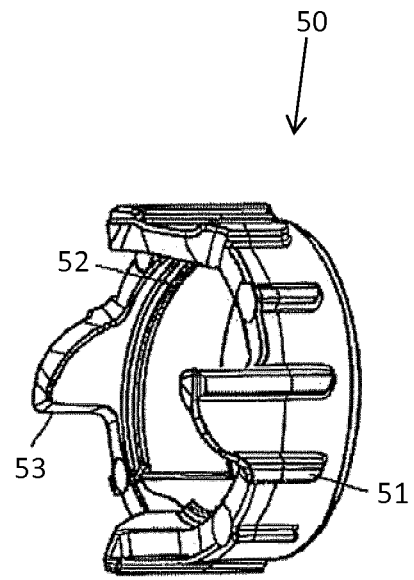
FIG. 7 shows an isolated view a last dose nut.

The coupler 143 shown in FIG. 6 rotationally couples the two halves of the drive sleeve 140 together during dialing and dispense, whilst allowing them to de-couple during reset. The coupler 143 has to also transfer the last dose stop load from the proximal drive sleeve 142 to the distal drive sleeve 141. Two sets of teeth are provided in the coupler 143 for engaging teeth 146 and teeth 147, respectively. The coupler 143 is snapped onto distal drive sleeve 141 allowing limited relative axial movement with respect to the proximal drive sleeve 142.

The last dose nut 50 is provided between the inner body 20 and the distal drive sleeve 141 of driver 140. Stop faces 53 are located on the proximal face of last dose nut 50 to limit the number of units that can be dialed if the stop faces 53 contact stops 145 of distal drive sleeve 141. The function of the last dose nut 50 is to prevent the user from dialing beyond a finite amount. This limit is based on the dispensable volume of the cartridge 80 and when reached, the user must replace the cartridge 80 and reset the device.

External ribs 51 of the last dose nut 50 engage splines 22 of inner body 20. An internal thread 52 of the nut engages the external thread 144 of distal drive sleeve 141. As an alternative, splines and ribs could be provided on the interface between the nut 50 and the driver 140 and threads could be provided on the interface between the nut 50 and the inner body 20. As a further alternative, the nut 50 may be designed as e.g. a half nut.

The display member 160 is a generally tubular element which is composed of a number sleeve 161 and dial sleeve 162 which are snapped together during assembly to axially and rotationally constrain these two components, which thus act as a single part. The dial sleeve 162 is assembled to the number sleeve 161 such that once assembled, no relative movement is allowed. The parts are made as separate components to enable both molding and assembly. Also, whereas the number sleeve 161 is preferably white to give contrast for the e.g. black dose numbers, the dial sleeve 162 color can be chosen to suit the aesthetics or perhaps to distinguish the drug type.

At the proximal end, the dial sleeve 162 has internal clutch features 165 that engage with the clutch sleeve 90 during dialing and disengage from the clutch during dispense. These clutch features 165 rotationally lock the dial sleeve 162 to the clutch sleeve 90 during dialing and when the zero and maximum dose stops are engaged. When the dose member 70 is depressed these clutch features disengage to allow the clutch sleeve 90 to move axially whilst the dial sleeve 162 and number sleeve 161 spin back to the zero unit start position.

Figure 4:
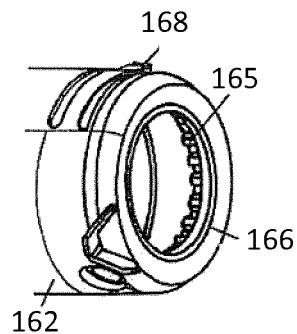
FIG. 4 shows a proximal end of the display member according to FIG. 2.
Figure 5:
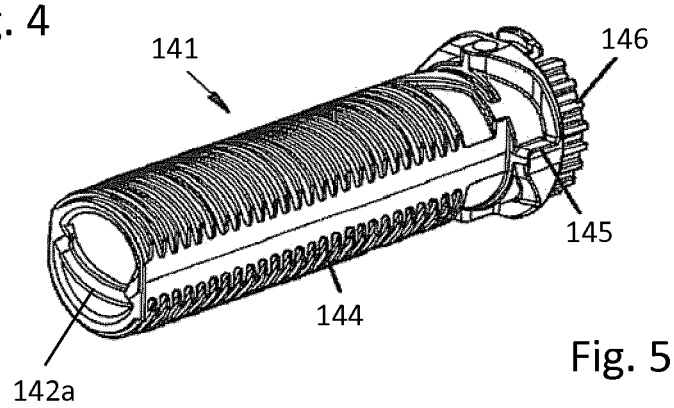
FIG. 5 is an isolated view of a distal driver part according to FIG. 2.

The dial sleeve 162 rotates out during dialing through its engagement with the clutch sleeve 90 and number sleeve 161, and rotates back in during dispense under the axial force applied by the proximal drive sleeve 142 to a flange-like bearing face 166 on the proximal end of the dial sleeve as shown in FIG. 4. This bearing face 166 engages with the flexible arms 148 of the proximal drive sleeve 142 during dispense. Two diametrically opposite faces 167 may engage with the outer body 10 when the maximum dose has been dialed, to form the maximum dose stop faces. Alternatively, a maximum dose stop may be also formed between the inner body 20 and the display member 160.

A central sleeve-like portion of the dose member 70 is provided with four arms 73 having hook-like snap features 74 at their respective distal ends. The arms 73 form splined surfaces engaging with the clutch sleeve 90 to transfer torque from the dose member 70 through the clutch to the dial sleeve 162 and proximal drive sleeve 142. The snap features 74 engage apertures in the clutch sleeve 90 and are designed with angled undercut faces to maintain engagement when an axial load is applied to pull the dose member 70 out of the pen body 10. The space between arms 73 defines pockets giving clearance for the flexible arms 148 of proximal drive sleeve 142 to slide freely relative to the dose member 70 and clutch sleeve 90 when the dose member 70 is depressed to release the clutch during dose dispense.

The tubular clutch sleeve 90 is provided between the display member 160 and the dose member 70. The clutch sleeve 90 is fixed relative to and retains the dose member 70 and together they travel axially relative to the proximal drive sleeve 142 when the dose member 70 is depressed during dispense, disengaging the clutch teeth 95 from the dial sleeve clutch teeth 165. The clutch sleeve 90 also transfers torque from the dose member 70 to the proximal drive sleeve 142, and the dialing and zero and maximum dose stop loads from the dose member 70 via the clutch teeth to the dial sleeve 162 and number sleeve 161.

Splines 91 provided on an inner surface of the clutch sleeve 90 engage with the proximal drive sleeve 142. At the distal end face, clutch biasing teeth 92 are provided which mate with similar teeth 109 on the proximal clicker part 102 to ensure that in the unrestrained button out position (dialed dose) the clutch is biased in rotation to the proximal clicker part 102 under the biasing action of the clutch spring 103 thus ensuring that the dose number shown on the display member is correctly and unambiguously displayed to the user. The teeth 92 are shallow in height to prevent the proximal clicker part 102 from engaging with splines on the proximal drive sleeve 42 during dialing. Four snap apertures 93 serve to retain the snap features 74 of the dose member 70. Near its proximal end, the clutch sleeve 90 has splines 94 which at the end of dispense with the dose member 70 depressed, lock to the inner body 20 to prevent the user from rotating the dose member 70 below the zero dose position.

Clutch teeth 95 engage with clutch teeth 165 of the dial sleeve 162 to rotationally couple the dose member 70 via the clutch to the number sleeve 161. During dispense the clutch sleeve 90 is moved axially and distally so as to disengage these clutch teeth 95 releasing the dial sleeve 162 to rotate back into the device whilst the clutch sleeve 90 and hence driver 140 move axially to dispense the dose.

The clicker 100 comprises a distal clicker part 101, a proximal clicker part 102 and a spring 103. The spring 103 serves to bias the dose member 70 so that at the end of a dispense operation the dose member 70 moves axially in the proximal direction, re-engaging the clutch sleeve 90 with the dial sleeve 162 ready for dialing. Further, it provides the spring force for the clicker components to provide audible and tactile feedback to the user and also provides detent positions for the number sleeve 161. In addition, it holds the two halves of the drive sleeves 141, 142 in rotational engagement during dialing and dispense, whilst allowing them to disengage during device reset.

The distal clicker part 101 is permanently splined to the proximal drive sleeve 142 and engages with the proximal clicker part 102 which in turn is splined and hence rotationally locked but axially displaceable to the inner body 20. During dialing when the driver 140 is rotated relative to the inner body 20, the two clickers 101, 102, rotate relative to each other under the compression force of the clutch spring 103. This force acting through with the clicker teeth formed on the end face of each clicker provides the clicks and also the detent dialing positions During dispense the two clickers 101, 102 are pressed together under the axial dispense load applied by the user to the dose member 70 and this prevents relative rotation between the proximal drive sleeve 142 and inner body 20, driving the piston rod 30 forwards to deliver the dose. The splines 104 on the inner bore rotationally couple the distal clicker part 101 to the proximal drive sleeve 142 at all times, but allow free axial movement when the dose member 70 is depressed during dispense and when the two clickers ride over each other during dialing. The profile of the clicker teeth 105, 106 on both distal clicker part 101 and proximal clicker part 102 are identical and ride over each other under the compressive load from the spring 103 during dialing.

The proximal clicker part 102 is permanently splined to the inner body 20 by external splines 107 which prevent relative rotation with the inner body 20 during both dialing and dispense, providing clicks during dialing and locking the proximal drive sleeve 142 in rotation during dispense. Additional cylindrically shaped splines 108 also couple the proximal clicker part 102 rotationally to the proximal drive sleeve 142 when the dose member 70 is depressed, this preventing the user from dialing past 80 units with the dose member 70 depressed. Proximal clicker part 102, in addition to the primary clicker teeth 106, has clutch biasing teeth 109 on the opposite end face. These teeth mate with similar teeth 92 on the clutch sleeve 90 to ensure that in the unrestrained button out position (dialed dose) the clutch is biased in rotation by the proximal clicker part 102 under the biasing action of clutch spring 103.

The cartridge bias spring 110 is assembled as two components one after the other, the lower first and the upper second. The spring combination serves to apply an end load to the cartridge 80 so as to bias it forwards onto the end face of the ferrule in the cartridge holder 11. This ensures that when the user removes and attaches a needle, the friction between the needle cannula and septum of the cartridge 80 does not move the cartridge 80 axially relative to the cartridge holder 11. The bias spring 110 also acts to provide a force against which the user has to connect the cartridge holder 11 and this may add to the tactile feedback of a bayonet joint between cartridge holder 11 and inner body 20. The spring 100 also serves to eject the cartridge holder 11 if the cartridge holder is not correctly attached in a secure position, highlighting this error to the user.

During dose setting the dose member 70, driver 140 and display member 160 are rotationally locked together via clutch sleeve 90. Further, dose member 70, driver 140 and display member 160 are axially coupled. Thus, these three components wind out of the outer body 12 during dose setting. Clockwise rotation of the dose member 70, i.e. rotation of the dose dial 71 causes the driver 140 to rotate on a helical path and in doing so it advances along the piston rod 30 which remains fixed throughout dialing. The clicker arrangement 100 provides tactile and audible feedback to the user when dialing doses. At the maximum settable dose of 80 units, stop features engage to prevent further dialing.

With the desired dose dialed, the device 1 is ready for dose dispensing. This requires pushing the proximal button portion of the dose member 70 which will result in a disengagement of the clutch sleeve 90 from dial sleeve 162 thus allowing relative rotation between the display member 160 and the dose member 70. In all conditions the driver 140 and the dose member 70 are rotationally locked together by engagement of arms 73 and fingers 148 and by splines 91 engaging corresponding splines on proximal drive sleeve 142. Thus, with the clutch sleeve 90 disengaged dose member 70 and driver 140 are rotationally locked together with the dose member 70, the driver 140 and the display member 160 still being axially coupled.

When dispensing a dose, the dose member 70 and clutch sleeve 90 are moved axially relative to the mechanism compressing the clutch spring 103. Because the proximal clicker part 102 is splined to the inner body 20 and the axial load passing through the clicker teeth 105, 106 locks the distal clicker part 101 in rotation to the proximal clicker part 102, the drive sleeve 140 and clutch sleeve 90 parts of the mechanism are rotationally locked to the inner body 20 and are thus forced to move axially whilst the dial sleeve 162 and number sleeve 161 are free to spin back into the outer housing 10. The interaction of mating threads between the piston rod 30, driver 140 and inner body 20 delivers a mechanical advantage, for example of 2:1.

In other words, axially advancing driver 140 causes the piston rod 30 to rotate which due to the threaded engagement of piston rod 30 with the inner body 20 advances the piston rod 30. During dose dispensing dispense clicker 168, 71 is active which involves dose member 70 and display member 160. The dispense clicker provides primarily audible feedback to the user that the medicament is being dispensed.

When dispensing of a dose is complete and when the user removes the force from the end of the dose member 70, the clutch spring 103 pushes this dose member 70 proximally, re-engaging the teeth 165 and 95 between the clutch sleeve and the dial sleeve.

Resetting the device starts with removal of the cartridge holder 11 and replacing an empty cartridge with a full cartridge 80. As the cartridge holder 11 is re-attached, the bung of the new cartridge 80 contacts bearing 33, thus pushing piston rod 30 back into the housing. Initially, the piston rod 30 screws into the inner body 20, thereby axially disengaging the coupler 143 from the proximal drive sleeve 142 against the biasing force of spring 103. Once disengaged the coupler 143 is free to start rotating together with distal drive sleeve 141 and continues to do so as the cartridge holder 11 is moved axially into engagement with the inner body 20. Thus, the distal drive sleeve 141 rotates with respect to the proximal drive sleeve 142 which is still rotationally constrained in inner body 20 as clicker parts 101 and 102 are pressed together by compressed spring 103.

As the distal drive sleeve 141 rotates, last dose nut 50 is reset to its (distal) start position. Coupling the cartridge holder 11 to inner body 20 backs off the mechanism due to the bayonet structure allowing re-engagement of the proximal drive sleeve 142 with coupler 143 and thus the distal drive sleeve 141.

A zero unit rotational hard stop 164 is provided at a distal end of the display member 160, in particular at the distal end of its number sleeve 161. This stop 164 axially and/or circumferentially abuts with a stop 24 formed on the outer circumference of the inner body 20. Correspondingly and in proximal direction 5 the thread 21 is terminated by a proximal stop 25 that may engage with the inner thread 163 or a stop feature provided on the inside of the number sleeve 161. A proximal or maximum dose stop may be also located on an inside of the proximal housing 12 to engage with a axially extending stop feature 167 at a proximal end of the number sleeve 161.

Figure 14:
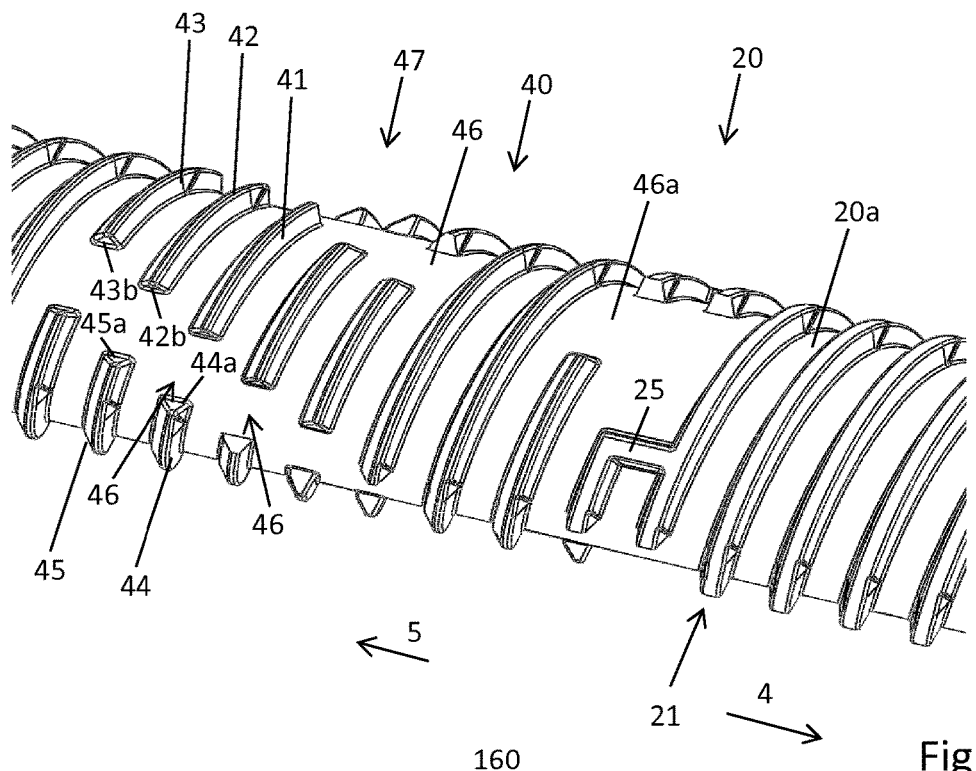
FIG. 14 is a perspective illustration of part of an inner body.
Figure 15:
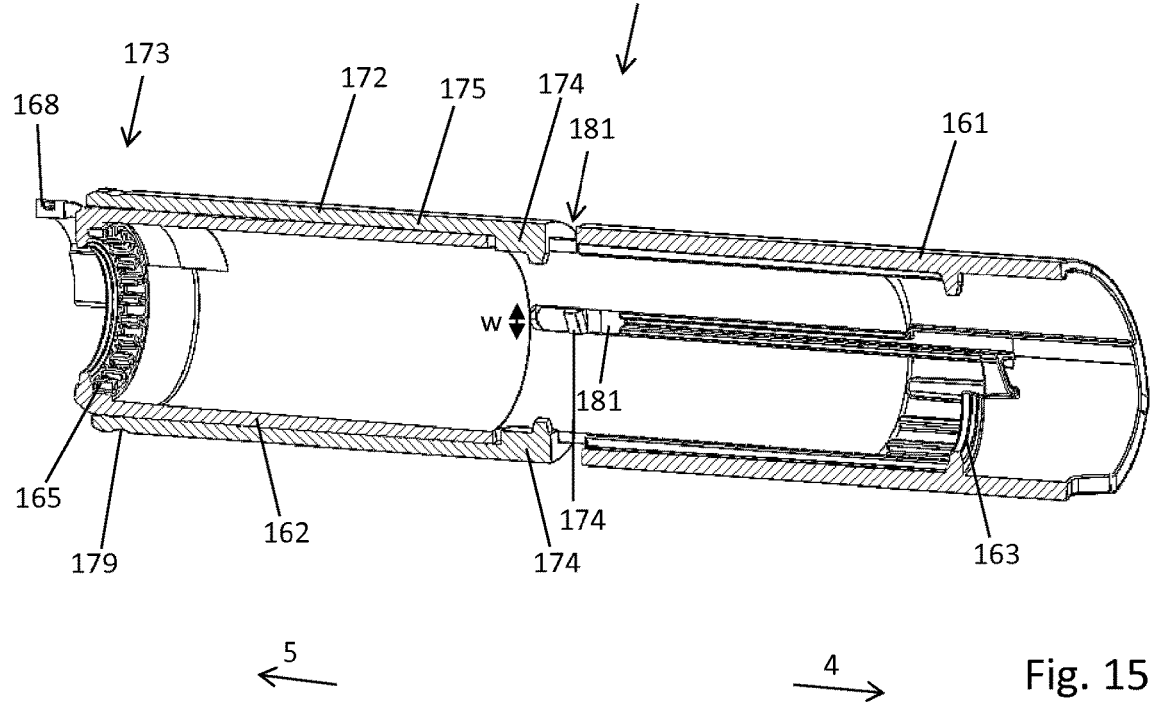
FIG. 15 shows a longitudinal cross-section of a first embodiment of the display member engaged with a blocking sleeve.
Figure 16:
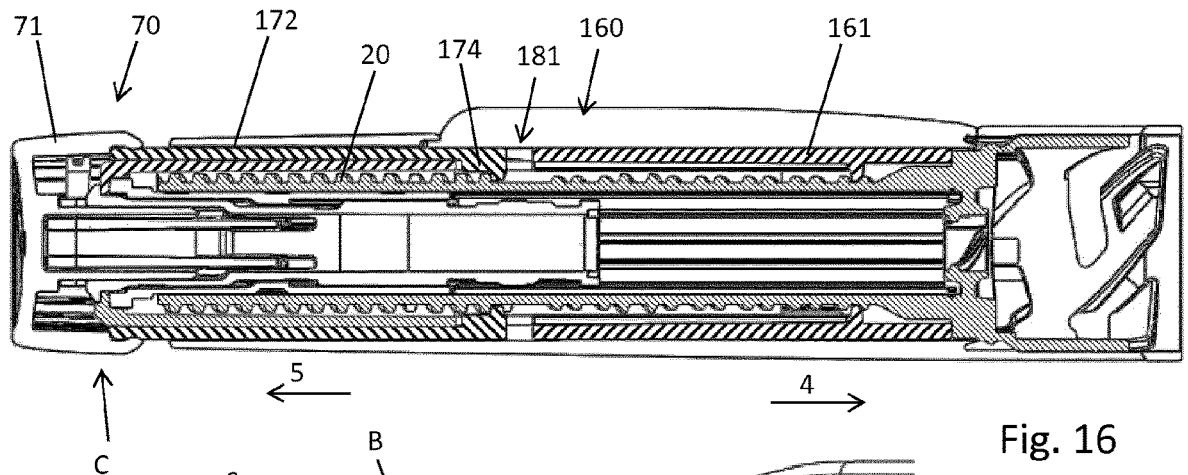
FIG. 16 is a longitudinal cross-section of a drive mechanism according to FIG. 15.

As it is apparent from FIGS. 14 and 16, the inner body 20 comprises an elongated shaft 20a. Along the outer circumference of the elongated shaft 20a there is provided an outer thread 21 by way of which the inner body 20 is threadedly engaged with a radially inwardly extending thread feature or inner thread 163 of the display member 160 as shown in the cross-section in FIG. 15. In the present embodiment the outer thread 21 is located in a distal portion of the inner body 20. The elongated shaft 20a and hence the inner body 20 further comprises a blocking structure 40. In the present embodiment the blocking structure 40 is located at a proximal portion of the elongated shaft 20a. It is also located on the outer circumference of the elongated tubular shaft 20a. As it is apparent from FIG. 14, the outer thread 21 and the blocking structure 40 are axially separated. Hence, the outer thread 21 and the blocking structure 40 are axially non-overlapping.

The blocking structure 40 comprises or forms at least one blocking thread 47. The blocking thread 47 and the outer thread 21 have the same pitch and are of the same lead. It is in principle also possible that the axial positions of outer thread 21 and blocking structure 40 interchange so that the outer thread 21 is located at a proximal end of the elongated shaft 20a and that the blocking structure 40 is located at a distal end of the shaft 20a. Moreover the blocking structure 40 and the outer thread 21 could also be arranged at least partially overlapping in the axial direction. Hence, the blocking structure 40 or the blocking thread 47 may be located axially in between successive convolutions of the outer thread 21 and vice versa.

The display member 160 and in particular the dial sleeve 162 thereof comprises a radially inwardly directed stepped down portion at its proximal end and is hence selectively rotationally engageable with the clutch sleeve 90, which in turn is axially fixed to the dose member 70. Via said clutch sleeve 90 and the mutually engaging teeth 95 or clutch features 165 the dose member 70 is selectively rotationally engageable with the dial sleeve 162 and hence with the display member 160. In this way a clutch C between the dose member 70 and the display member 160 is provided. As shown in FIG. 16 the dose member 70 comprises a dose button 71 or dose dial that is axially fixed to a blocking sleeve 172. The tubular blocking sleeve 172 extends in an axial direction and is located outside the dial sleeve 162. The dial sleeve 162 and the number sleeve 161 of the display member 160 are rigidly attached and mutually fastened. The blocking sleeve 172 surrounding at least a portion of the dial sleeve 162 is displaceable in an axial direction relative to the display member 160, hence relative to the number sleeve 161 and to the dial sleeve 162 at least by a predefined axial distance.

The blocking sleeve 172 encloses a proximal portion of the display member 160. The blocking sleeve 172 encloses the dial sleeve 162. The blocking sleeve further comprises numerous blocking elements 174 extending radially inwardly from a sidewall 175 of the blocking sleeve 172. The tubular sidewall 180 of the display member 160, e.g. the sidewall 180 of the number sleeve 161 comprises numerous apertures 181 or recesses at or near its proximal end. The tangential width of these apertures 181 matches with the tangential width or tangential size of the blocking elements 174 located at the distal end of the blocking sleeve 172 and extending radially inwardly through the apertures 181. The apertures 181 are configured as longitudinal slits through which the blocking elements 174 extend radially inwardly and in which the blocking elements 174 are allowed to slide in an axial direction.

The blocking elements 174 are rigidly fastened to the inside of, or formed integrally with the blocking sleeve 172. In the present embodiment there are provided four blocking elements 174 that are equidistantly arranged in circumferential direction and that are located in a common lateral plane perpendicular to the longitudinal elongation of the blocking sleeve 172. In this way the blocking sleeve 172 is axially displaceable relative to the display member 160 to such an extent that matches with the axial dimensions of the apertures 181.

At the proximal end 173 of the blocking sleeve 172 there is provided an annular groove 179 on the outer circumference of the blocking sleeve 172. By means of this groove 179 the dose member 70, in particular the generally cylindrical part of the dose dial 71 is clip fastened to the blocking sleeve 172. The mutual connection of the dose member 70 and the blocking sleeve 172 is rigid in the axial direction but allows for a relative rotation of the dose member 70 and the blocking sleeve 172. Since the circumferential width of the radially inwardly protruding blocking elements 174 matches with or is substantially equal to the circumferential width of the aperture 181 a rotational coupling and hence a permanent and rigid torque transferring connection between the blocking sleeve 172 and the display member 160 is obtained.

As it can be further seen from FIG. 15 the dial sleeve 162 has a reduced outer diameter compared to the diameter of the number sleeve 161. The outer diameter of the sidewall 175 of the blocking sleeve 172 is substantially equal to the outer diameter of the sidewall 180 of the number sleeve 161. The radial extension of the blocking element 174 is substantially equal to the radial extension of the inner thread 163.

By means of the blocking element 174 the blocking sleeve 172 can be snapped or clip fastened to the various apertures 181 of the dose member 160. In this way a permanent rotational engagement and rotational coupling between the display member 160 and the blocking sleeve 172 is obtained. At a radially innermost section the blocking element 174 comprises a radially inwardly extending protrusion 177.

An exemplary blocking structure 40 is shown in more detail in FIG. 14. The blocking thread 47 is interrupted or intersected by various gaps 46 extending between numerous blocking segments of which only blocking segments 41, 42, 43, 44 and 45 are denoted with reference numbers. The blocking segments 41, 42, 43, 44, 45 belong to the blocking thread 47 and constitute or form the intersected blocking thread 47. The blocking segments 42, 45 are aligned in tangential direction in accordance to the pitch of the blocking thread 47. Tangentially between a tangential end 42b of the blocking segment 42 and a tangential end 45a of the consecutive or neighboring blocking segment 45 there is provided a gap 46 having a predefined tangential or circumferential size. The tangential gap size 46 is at least as large as the tangential width w of the radially inwardly extending blocking elements 174.

Likewise the blocking segments 42, 45 two further blocking segments 41, 44 that are also separated at their tangential ends 41b, 44a by a gap 46 are located axially offset from the blocking segments 42, 45. The gaps 46 between the blocking segments 42 and 45 and between the blocking segments 41 and 44 are somewhat tangentially or circumferentially offset. The axial as well as circumferential position and size of the gaps 46 define discrete dose sizes or a range of a minimum and a maximum dose that can be set and dispensed by the drive mechanism 2. In an initial or zero dose configuration the blocking elements 174 of the blocking sleeve 172 are located near a distal end of the blocking thread 47.

Near a distal end of the blocking structure 40 there is provided an initial gap 46a. At the end of a dose dispensing procedure the blocking elements 174 and in particular their protrusions 177 will be co-aligned with this initial gap 46a so as to allow and to support a proximally directed returning of the dose member 70 towards its dose setting position S.

Figure 17:
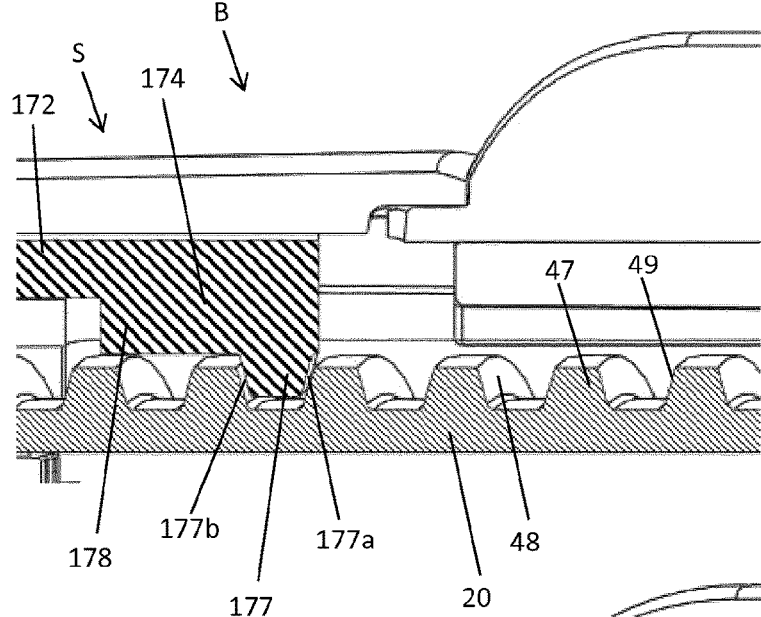
FIG. 17 is an enlarged view of FIG. 16 with the blocking sleeve in a blocking configuration with the blocking structure.

As a dose is dialed the blocking sleeve 172 rotates in unison with the display member 160. Consequently and according to the specific geometric design of the blocking structure 40 the blocking elements 174 are located axially offset from the various blocking segments 41, 42, 43, 44, 45 of the blocking structure 40. When dialing a dose as shown in FIG. 17 the protrusions 177 of the blocking elements 174 are located axially between two axially consecutive convolutions of the blocking thread 47. In typical embodiments a distally facing beveled edge 177a of the blocking elements 174 is located in close proximity to the proximal edge 49 of the blocking thread 47. The distal edge 177a may even be or come into a gentle contact arrangement with the blocking thread 47. Due to an identical pitch of the outer thread 21 and the blocking thread 47 and due to the axial coupling between the display member 160 and the dose member 70 via the clutch sleeve 90 the blocking elements 174 remain in a constant proximal position relative to the blocking thread 47 as the blocking sleeve 172 is subject to a dose dialing rotation.

Figure 18:
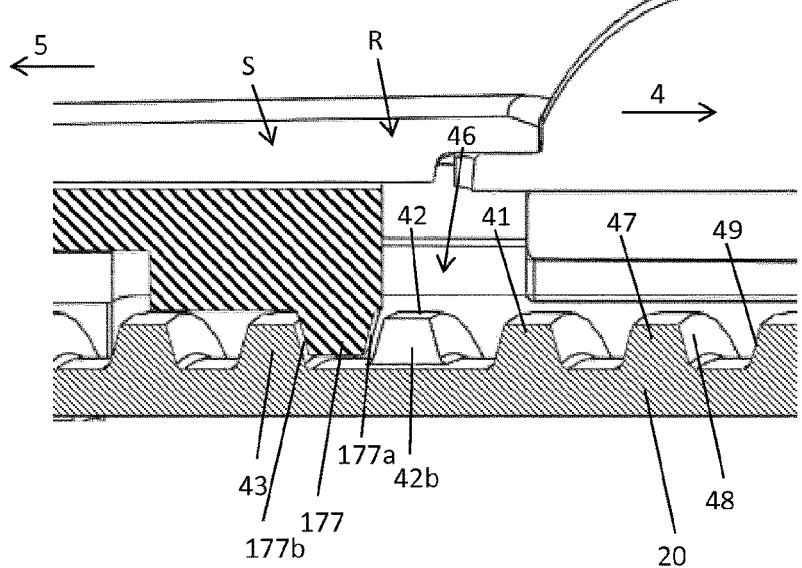
FIG. 18 is another enlarged view of the engagement of the blocking sleeve with the blocking structure in a release configuration and FIG. 19 is an enlarged cross-section of the blocking sleeve and the blocking structure during dose dispensing.
Figures 19, 20:
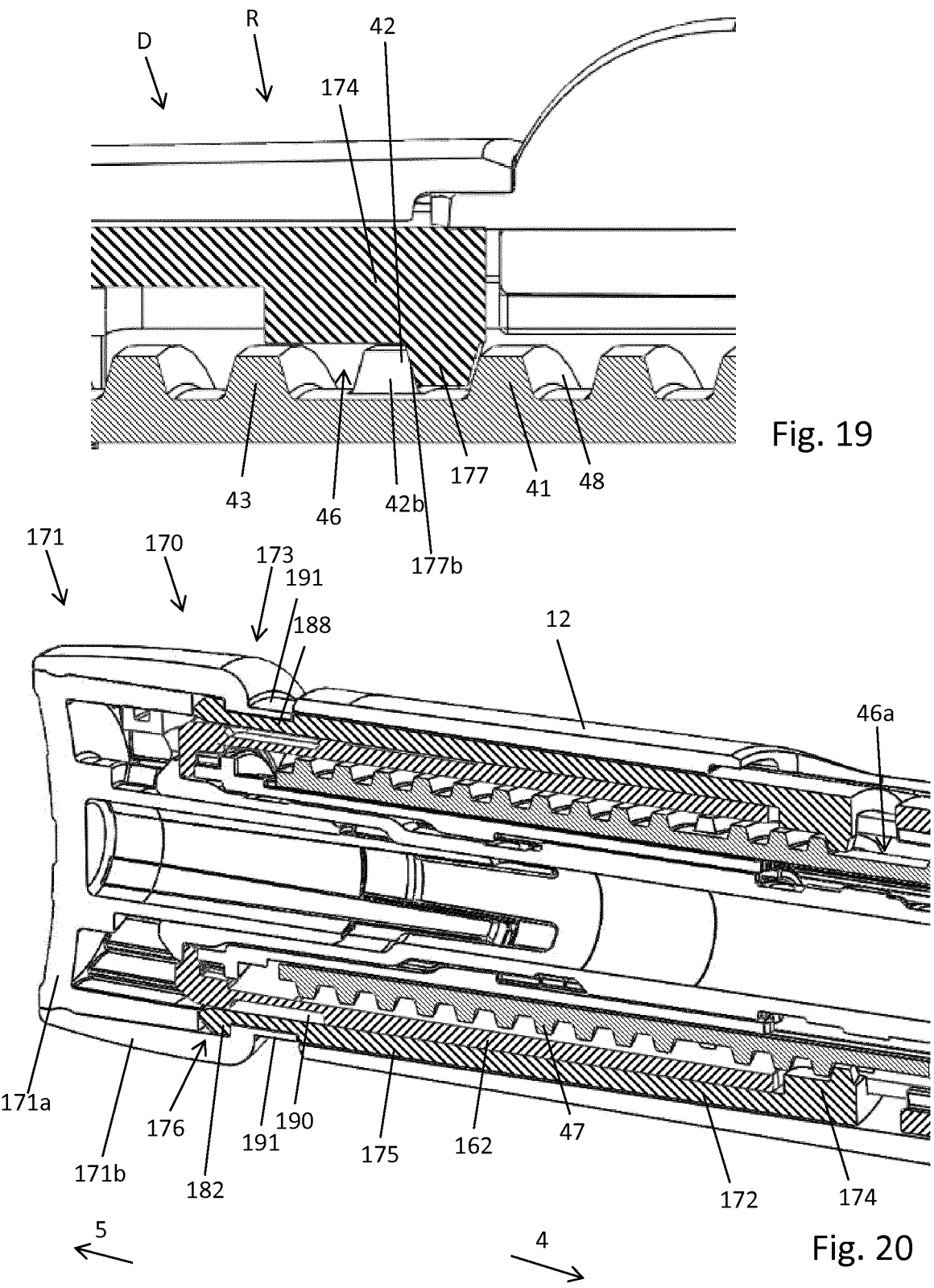
FIG. 20 is a longitudinal cross-section of another embodiment of the drive mechanism with the dose member comprising a button part and a dial part.
Figure 21:
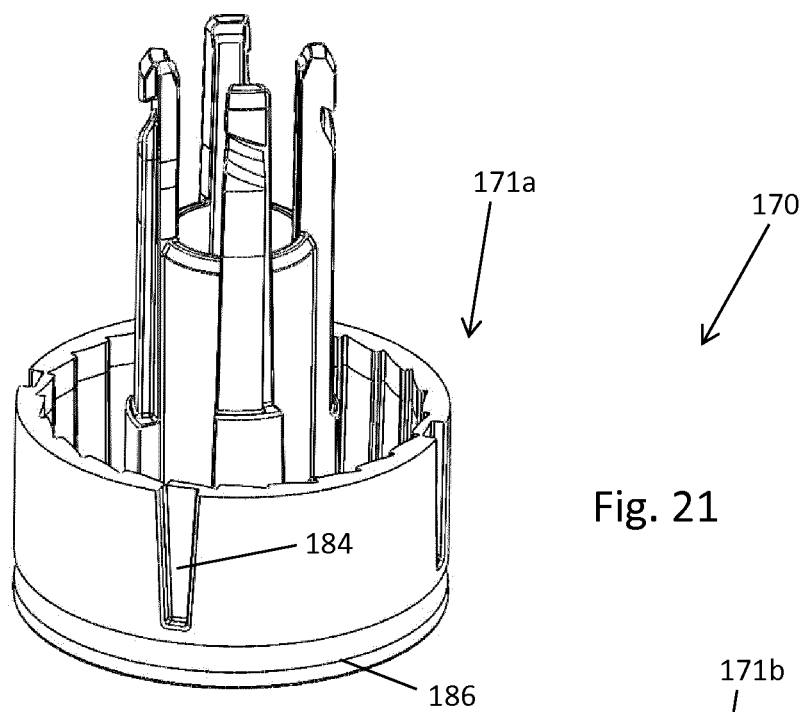
FIG. 21 is an isolated perspective view of the button part.

At the end of a dose setting or dose dialing procedure the blocking elements 174 may either be located in a position at least partially tangentially and radially overlapping with a distally located blocking segment 41, 42, 43, 44 or 45 or the blocking elements 174 align with or may be located with their complete tangential size inside the at least one gap 46. In the latter case the dose member 70 and the blocking elements 174 of the blocking sleeve 172 are in a release position R as shown in FIG. 18. As the blocking elements 174 are axially aligned with respective gaps 46 of the blocking structure 40 the blocking structure 40 allows and enables a distally directed axial displacement of the blocking elements 174 relative to the blocking structure 40. As it is shown in FIG. 19 the blocking elements 174 have axially displaced through the gap 46 such that the innermost protrusions 177 of the blocking elements 174 traverse and pass by a longitudinal end 42b of a blocking segment 42.

Due to the distally directed axial displacement of the blocking sleeve 172 the clutch C is allowed to disengage, thereby switching the drive mechanism 2 into the dose dispensing mode D. During dose dispensing a user constantly applies distally directed pressure or thrust to the dose button 71. Under this force and due to the mutual interaction of the dose member 70, the driver 140, the inner body 20 and the display member 160 the display member starts 160 to rotate in a dose decrementing direction so that dose size indicators, such as numbers printed on the outer circumference of the number sleeve 161 appear in a decreasing order in the window 14 of the proximal housing part 12. In the event that dose dispensing is interrupted the spring 103 tends to displace the clutch sleeve 90 and the dose member 70 back into the proximal end position.

When the blocking sleeve 172 is subject to a rotation during dispensing procedure the blocking elements 174 thereof enter the free space between axially neighboring blocking segments 42 and 41. A proximal edge 177b of the protrusion 177 will then be located distally from the distal edge 48 of the blocking thread 47. If a user should interrupt a dispensing procedure by releasing the dose member 70 the proximal edge 177b of the blocking element 174 axially abuts with the distal edge 48 of the blocking thread 47. A returning of the dose member 70 into its proximal dose setting position is therefore also blocked. The clutch C between the dose member 70 and the display member 160 remains decoupled. The clutch C does not re-engage and the user is therefore not be able to change the dose as it was initially set.

Resuming the dose dispensing is immediately possible as the user depresses the dose button 71 again in distal direction 4. Since the blocking element 174 did not traverse the blocking segment 42 in proximal direction 5 the dose member 70 remains in the dispensing position D.

In other configurations where a user selects or dials a dose that is not intended to be dispensed by the injection device 1 there will be at least a partial tangential and radial overlap of the protrusions 177 with one of the blocking segments 41, 42, 43, 44, 45 as seen in axial direction. If a user depresses the dose member 70 by pressing on the dose button 71 in distal direction 4 the mutually corresponding beveled edges 177a, 49 of the protrusions 177 and the blocking thread 47 will lead to an axial abutment as it is apparent from FIG. 17. Then the blocking element 174 and the blocking sleeve 172 are prevented from moving in distal direction 4 relative to the inner body 20 and hence relative to the display member 160.

In this way axial load applied to the dose member 70 via the dose button 71 is directly transferred in axial and distal direction 4 to the inner body 20.

Regarding this aspect it is of particular benefit when the blocking sleeve 172 comprises numerous blocking elements 174 that simultaneously engage with correspondingly-shaped blocking segments 41, 42, 43, 45 of the blocking structure 40. In this way axial load applied to the dose member 70 can be distributed over various load paths. The mechanical load present on each single blocking element 174 can be reduced. A likelihood of fracture or breakage of blocking elements 174 in the event that excessive distally directed pressure is applied to the dose member 70 can be reduced. Moreover, having the rigid and stiff blocking elements 174 located on the solid tubular blocking sleeve a rather stable and robust mutual engagement of the blocking elements 174 with the blocking structure 40 can be obtained.

As it is further apparent from FIGS. 17-19 each one of the blocking elements 174 comprises a base portion 178 with a rather elongated shape in axial direction. From a radially innermost end of the base portion 178 the protrusion 177 extends further radially inwardly. In the present embodiment it is only the protrusion 177 that enters the free space between consecutive convolutions or axially separated blocking segments 41, 42, 43 of the blocking thread 47.

The base portion 178 remains radially outside the blocking thread 47. By means of the base portion 178 the protrusion 177 and hence the innermost section of the blocking element 174 can be stabilized with regard to a deflection in axial direction. The base portion 178 acts as a kind of an axial strut to improve mechanical load transfer through the respective blocking element 174. In this way the blocking elements 174 comprise a rather rigid and solid structure. This is also beneficial for the process of assembly, where the blocking elements 174 have to slide over the outer circumference of the dial sleeve 162 until they snap into the apertures 181.

Figure 22:
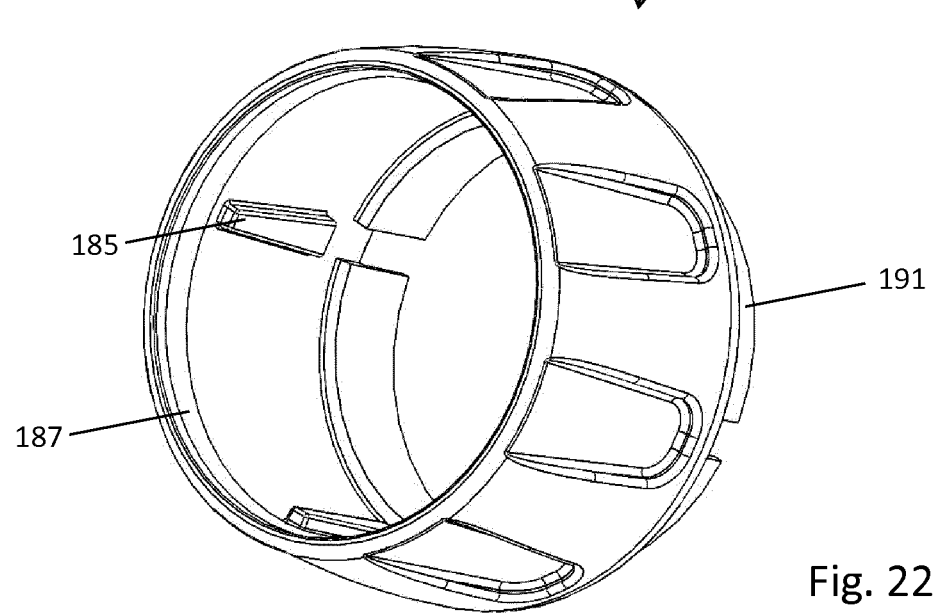
FIG. 22 is an isolated perspective view of the dial part.
Figure 23:
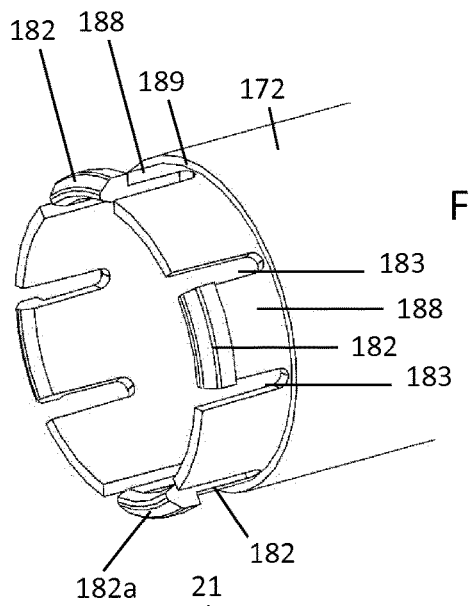
FIG. 23 is a perspective view of the proximal end of the blocking sleeve.
Figure 24:
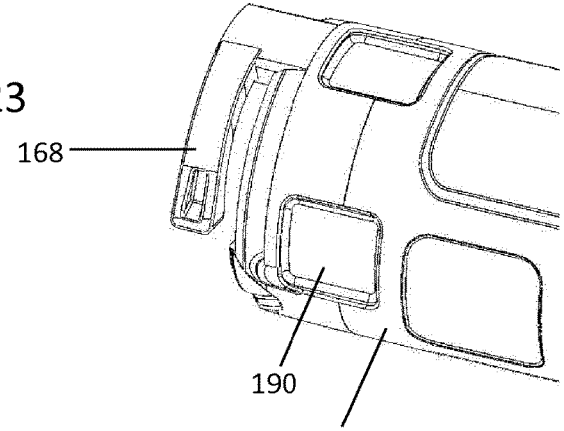
FIG. 24 is a perspective view of the proximal end of the display member.
Figure 25:
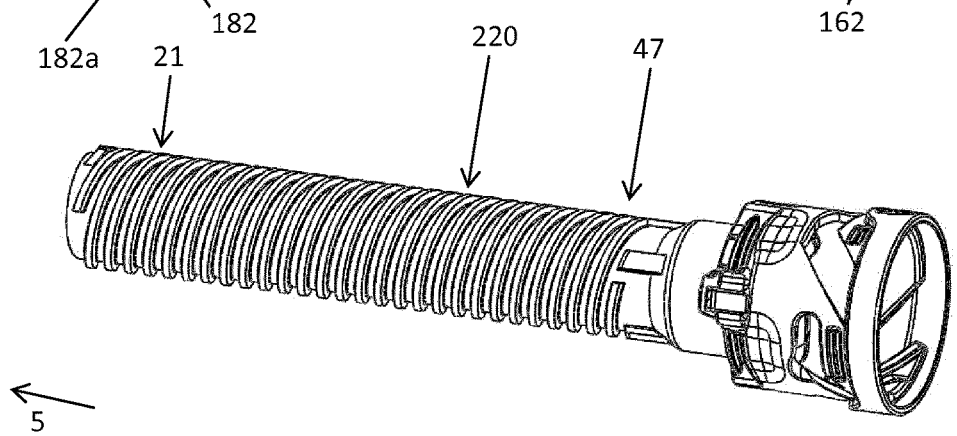
FIG. 25 shows another embodiment of the inner body with the outer thread located at a proximal end of the elongated shaft and with the blocking structure located at a distal portion of the elongated shaft.
Figure 26:
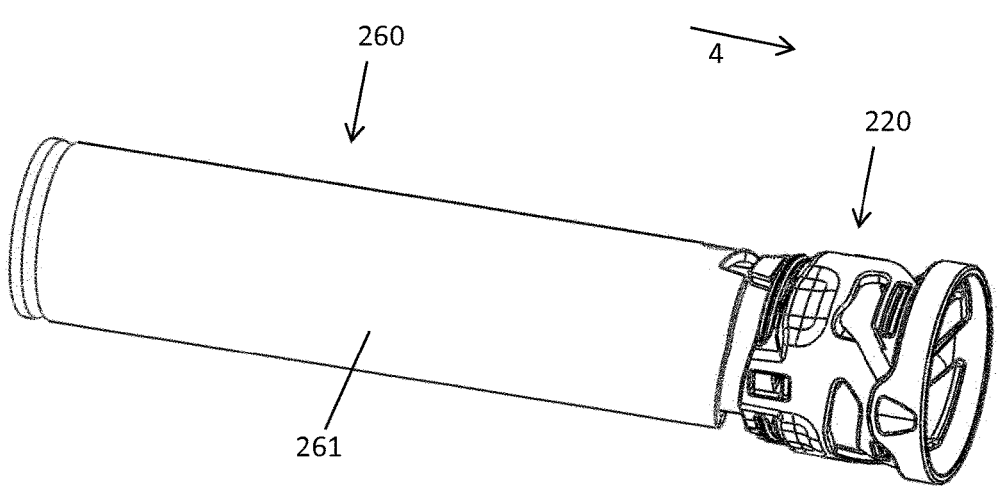
FIG. 26 is a perspective view of a pre-assembly of the inner body according to FIG. 25 and the display member.
Figure 27:
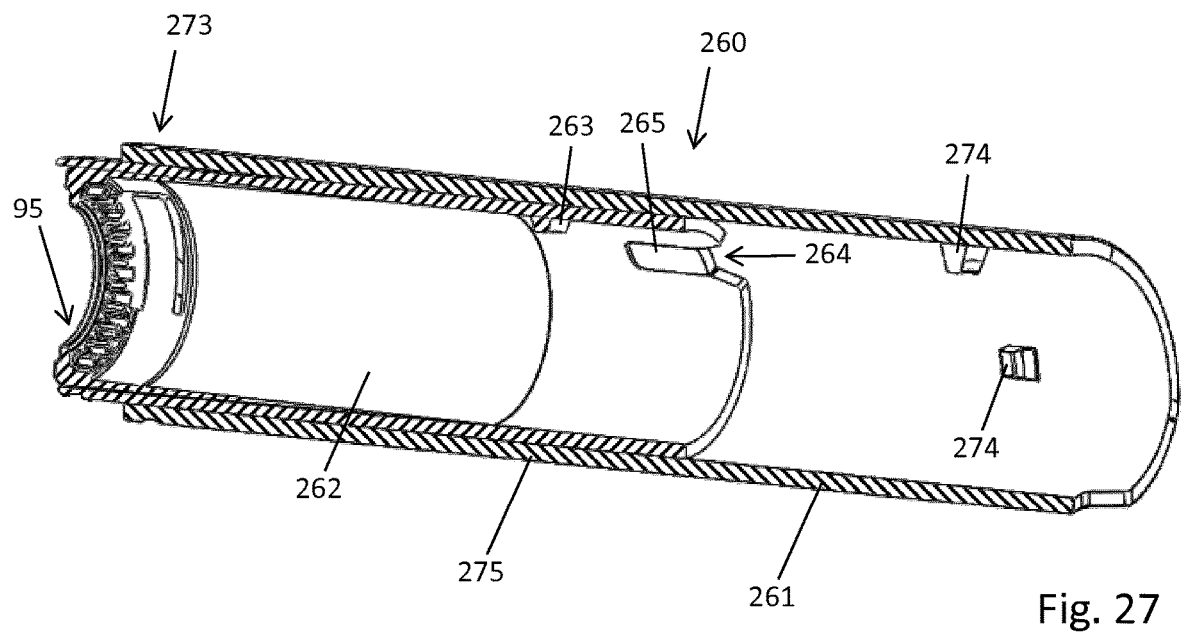
FIG. 27 is a longitudinal perspective cross-section through the display member according to FIG. 26
Figure 28:
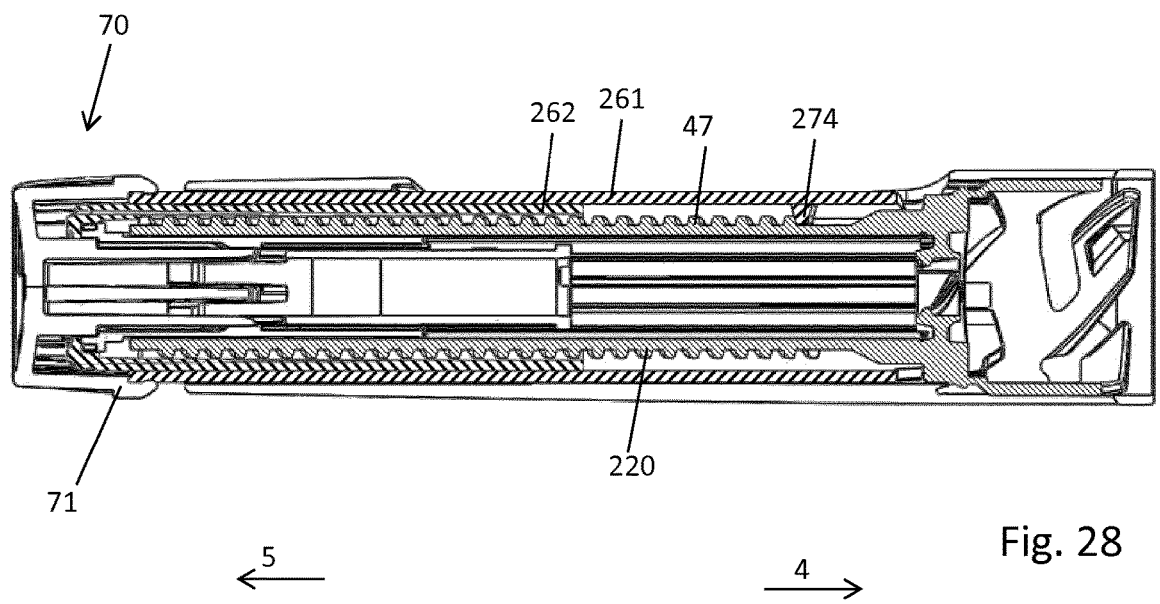
FIG. 28 is a longitudinal cross-section through the drive mechanism according to the embodiment of FIGS. 25-27.

In FIGS. 20-24 a further embodiment is illustrated that is functionally identical to the embodiment as described above with the exception of the connection between the dose button 171 and the display member 160. The blocking sleeve 172 as well as the display member 160 remain substantially unchanged compared to the embodiment as shown in FIGS. 14-15. Only at the proximal end 173 of the blocking sleeve 172 there are now provided numerous locking tabs 182 are configured act as positively engaging latching elements to engage with the dose button 171. As shown in FIG. 23 there are provided four axially extending locking tabs 182 that are separated by longitudinal slits 183.

This allows for a radial deflection of the locking tab 182 during assembly and during a fastening to the dose button 171. In the embodiment of FIGS. 20-24 the dose button 171 comprises a button part 171a and a dial part 171b. The button part 171a and the dial part 171b are positively engageable and fixable relative to each other. The button part 171a and the dial part 171b are axially as well as rotationally fixed. In a final assembly configuration of button part 171a and dial part 171b an annular fixing groove 176 is provided at the interior of the dose button 171 to receive the locking tabs 182 at the proximal end 173 of the blocking sleeve 172.

On the outer circumference of a cylindrical portion of the button part 171a and on an inside of the annular-shaped dial part 171b there are provided mutually corresponding and longitudinally extending recesses 184 and protrusions 185. In the present embodiment the recesses 184 are provided on the button part 171 and the corresponding protrusions 185 are provided on an inside of the dial part 171. When clipped and assembled together the mutually engaging protrusions 185 and recesses 184 provide a rigid rotational coupling of the button part 171a and the dial part 171b. Additionally, the proximal ends of the button part 171a and the dial part 171b comprise mutually corresponding annular protrusions and grooves. In this way a permanent axial engagement of the button part 171a and the dial part 171b can be obtained.

In the present embodiment the proximal end of the button part 171a is provided with annular recess 186 and the proximal end of the dial part 171b comprises a radially inwardly extending annular protrusion 187 to engage with the recess 186 as it is apparent from FIG. 20. By means of the recesses 184, 186 and the protrusions 185, 187 the dose button 171 can be pre-assembled prior to a final assembly with other components of the drive mechanism 2. In a pre-assembly configuration the dose button 171 can be assembled and fixed to the blocking sleeve 172.

For this the pre-assembled dose button 171 is simply clipped onto the proximal end 173 of the blocking sleeve 172 so that the locking tabs 182 supported by their beveled edges 182a deflect radially inwardly. Since the blocking sleeve 172 encloses the display member 160 and in particular the dial sleeve 162 a radially inwardly directed deflection of the locking tabs 182 is only possible when the locking tabs 182 overlap with pockets 190 on the outer circumference of the dial sleeve 162 as it is apparent from FIGS. 20 and 24. The proximal end of the locking tabs 182 is located proximally from the pockets 190. In such a dose setting configuration a radially inwardly directed deflection of the locking tabs 182 is hindered and prevented by the radial abutment with the dial sleeve 162.

By pushing the blocking sleeve 172 in distal direction 4 the locking tabs 182 substantially overlap with the pockets 190. The locking tabs 182 may then deflect radially inwardly into the pockets 190 thereby arriving in the fixing groove 176 on an inside facing sidewall portion of the pre-assembly of the button part 171a and the dial part 171b. As the nose-shaped locking tabs 182 arrive in the fixing groove 176 they return into their initial configuration and deflect radially outwardly. Consequently the locking tabs 182 leave the pockets 190 and align along the outer circumference of the dial sleeve 162.

As it is further apparent from FIGS. 20, 22 and 23 the locking tabs 182 comprise a radially recessed portion 188 that is located radially inwardly and axially offset to a stepped portion 189 of the tubular end of the blocking sleeve 172. This recessed portion 188 is configured to receive a distal but stepped down extension 191 of the dial part 171b. In this way the axial and distally directed extension or semicircular extensions 191 axially abut with the stepped portion 189 of the blocking sleeve 172. The outer circumference of the extensions 191 are flush with the outer circumference of the tubular shape of the blocking sleeve 172. When the dose button 171 is depressed in distal direction 4 to arrive at the dispensing position D the distal extensions 191 will be radially sandwiched between an inside of the proximal housing 12 and the recessed portion 188 of the locking tab 182. If the dose member 170 should be kept in the dispensing position, e.g. in the event that a dose dispensing procedure is interrupted the extensions 191 are hindered from deflecting radially outwardly and the snap connection of the dose button 171 with the blocking sleeve 172 cannot disengage even if rather large proximally directed forces should be applied to the dose button 171.

The fastening of the dose member 170 and in particular of the dose button 171 to the blocking sleeve 172 as it is shown in FIG. 20 is rather stable. This fastening structure is better able to withstand attempts to disconnect the dose button 171 from the device which is beneficial when a dose dispensing procedure is interrupted or paused at a dose size that is originally not intended to be selected and when the dose member 170 will not return into its proximal dose setting configuration because the blocking elements 174 are axially engaged with the blocking structure 40 as described above. Providing of a fixing groove 176 that is confined by the two components of the dose member 170 not only provides an improved resistance against proximally directed pull off forces applied to dose member 170 but also provides a more free-running rotational fit between the dose button 171 and the blocking sleeve 172. Since the blocking sleeve 172 rotates during dose dispensing while the dose button 171 is rotationally fixed a reduced friction between the dose button 171 and the blocking sleeve 172 is beneficial to reduce a dispensing force required to depress the dose button 171 in distal direction 4.

In FIGS. 25-28 another embodiment is illustrated with a slightly modified inner body 220. Compared to the inner body 20 as shown in FIG. 14 the axial positions of the outer thread 21 and the blocking structure 40 are swapped. Even though not shown in detail in FIG. 25 the blocking structure 40 is located on a distal portion of the inner body 220 and the outer thread 21 is located at a proximal portion of the inner body 220. Apart from that the configuration and function of the threaded connection between the inner body 20 and the display member 260 is somewhat similar or even identical to the embodiment as described above. Compared to the previous embodiment the functionality of the blocking sleeve 172 is implemented into a modified number sleeve 261 as it is apparent from the cross-section of FIG. 27.

It is actually the number sleeve 261 that comprises the radially inwardly protruding blocking elements 274 that engage with the blocking structure 47 of the inner body 220. Hence, the blocking sleeve 261 also acts as a number sleeve. The number sleeve or the blocking sleeve 261 therefore provides a double function. The dial sleeve 262 comprises an inner thread 263, e.g. in form of a thread segment that is threadedly engaged with the outer thread 21 of the inner body 220. In addition, the sidewall of the dial sleeve 262 comprises a longitudinal recess 264 or a through opening to receive a correspondingly-shaped longitudinally extending radial protrusion 265 located on the inside of the sidewall 275 of the blocking sleeve 261. By means of the mutual engagement of the recess 264 and the protrusion 265 the blocking sleeve 261 or number sleeve is permanently rotationally engaged and fixed to the dial sleeve 262.

The engagement of the recess 264 and the protrusion 265 further allows and supports a limited axial displacement of the blocking sleeve 261 relative to the dial sleeve 262 in order to allow for engagement and disengagement of the clutch C. Similar to already shown and described with regard to FIG. 16 the dose button 171 is clipped to the proximal end 273 of the blocking sleeve 261. An advantage of the embodiment according to FIGS. 25-28 is that in comparison to the embodiment of FIGS. 14-24 one fewer component is required. Since the blocking sleeve 261 or number sleeve is axially engaged with the dose button 171 the blocking sleeve 261 is subject to a small distally directed displacement relative to the housing 10 at the beginning of a dispensing procedure. Such an axial movement is only permitted if the blocking elements 274 are aligned with the gaps 46 of the blocking structure 40. Otherwise the axial engagement of the blocking elements 274 with blocking segments 41, 42, 43, 44, 45 of the blocking thread 47 prevents a distally directed displacement of the blocking sleeve 261 and hence of the dose button 171. The clutch C between the dial sleeve 262 and the clutch sleeve axially coupled to the dose button 171 cannot disengage and a dispensing procedure cannot be executed.

In FIGS. 29-32 a further embodiment of the drive mechanism 2 is shown. Here and in comparison to the embodiments of FIGS. 1-24 the functionality of the dial sleeve selectively rotationally engageable with the driver 140 of the drive mechanism 2 is provided by the blocking sleeve 362. Also here the blocking sleeve 362 encloses the number sleeve 361 which has numbers printed on its outer circumference. Similar to the embodiment shown in FIG. 15 it is the number sleeve 361 that is provided with an inner thread 363 by way of which the number sleeve 361 is threadedly engaged with the outer thread 21 of the elongated shaft 20a of the inner body 20. The inner body 20 of the embodiment according to FIGS. 29-32 is identical to the inner body 20 as shown in FIGS. 14 and 16.

Figure 31:
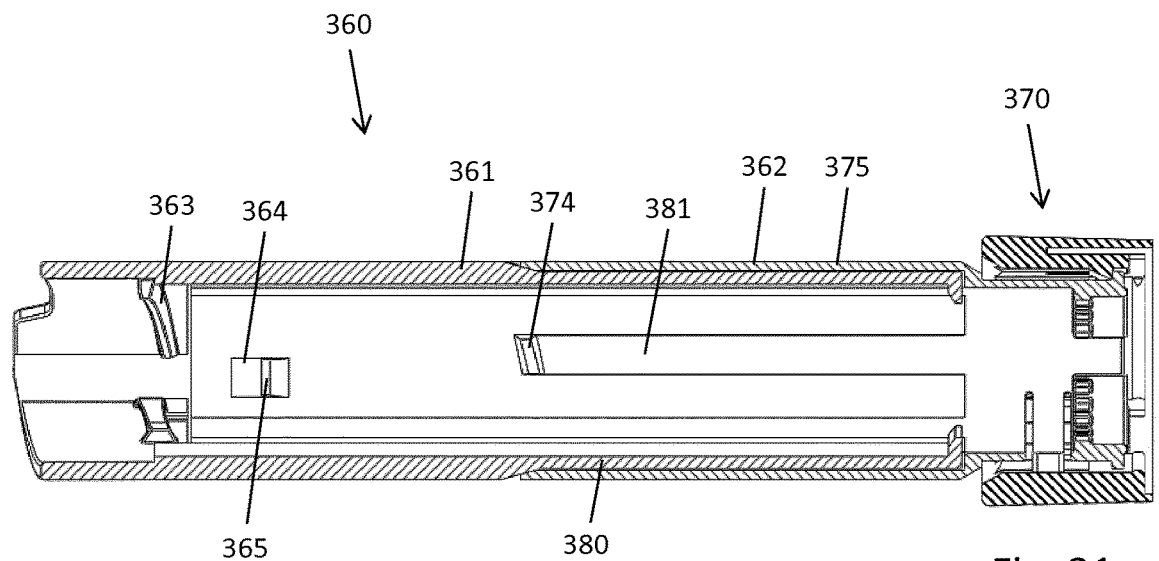
FIG. 31 is a longitudinal cross-section through the display member according to FIGS. 29 and 30 and FIG. 32 is a longitudinal cross-section through the drive mechanism according to the embodiment of FIGS. 29-31.

The number sleeve 361 and the blocking sleeve 362 are arranged in a rather convoluted way. They are clipped together so as to provide a permanent rotational engagement that allows for a limited axial displacement between the number sleeve 361 and the blocking sleeve 362. As shown in FIG. 31 the number sleeve 361 and the blocking sleeve 362 comprise at least one pair of recesses or apertures 364 mating with a correspondingly-shaped protrusion 365. Here, the recess 364 is provided in a sidewall of the number sleeve 361 and the radially inwardly extending protrusion 365 is provided on an inside of the blocking sleeve 362.

There is further provided at least one radially inwardly extending blocking element 374 on the inside of the sidewall 375 of the blocking sleeve 362. The blocking element 374 extends through an aperture 381 in the sidewall 380 of the number sleeve 361. In this way the blocking element 374 and hence the entire blocking sleeve 362 may engage with the blocking thread 47 in a way as described above. Also here the blocking sleeve 362 typically comprises a number of blocking elements 374 along the inner circumference of its sidewall 375. Correspondingly, the sidewall of the number sleeve 361 comprises a number of recesses 381.

Figure 32:
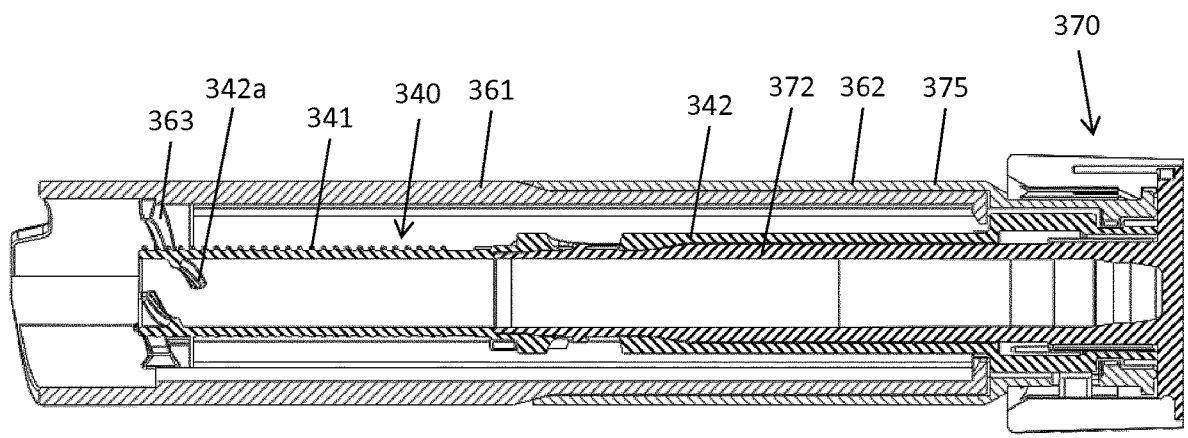

The driver 340 as shown in FIG. 32 is functionally equivalent to the driver 140 as shown in FIG. 2. It comprises a distal drive sleeve portion 341 and a proximal drive sleeve portion 342. In addition the driver 340 comprises an inner thread 342a to threadedly engage with the piston rod 30. As it is shown in greater detail in FIGS. 29 and 30 the dose member 370 and in particular the dose button 371 is axially fastened to the blocking sleeve 362. A radially inwardly extending latch element 377 axially engages with a radially outwardly extending flange-like rim 366 at the proximal end of the blocking sleeve 362.

In a proximal portion or at the proximal end actually overlapping with the dose button 371 the blocking sleeve 362 comprises a toothed structure 367 facing radially inwardly and being configured to engage in a torque transmissive way with a correspondingly-shaped toothed structure 343 on the outer circumference of the driver 340, in particular on the outer circumference at the proximal end of the proximal drive sleeve 342. The dose button 371 comprises a planar-shaped button part 371a. An inside and a distally facing portion of the button part 371a is in permanent axial abutment with a proximal end of the blocking sleeve 362. By means of the latch element 377 the dose button 371 and the blocking sleeve 362 are permanently axially fixed but are free to rotate relative to each other.

The dose button 371 comprises a tubular-shaped and axially extending dose sleeve portion 372 that is functionally equivalent or identical to the clutch sleeve 90 as described above. The dose sleeve portion 372 extends axially in a radial central area of the dose member 370 or of the dose button 371 and it is enclosed by the driver 340. The dose sleeve portion 372 is permanently rotationally engaged with the driver 340. In this way, any rotation of the dose button 371, in particular of its dial part 371b is transferred to a respective rotation of the driver 340 during dose setting. Due to the engagement of the toothed structures 343 and 367 this rotation of the driver 340 is also transferred to the blocking sleeve 362 and hence to the number sleeve 361.

Figure 29:
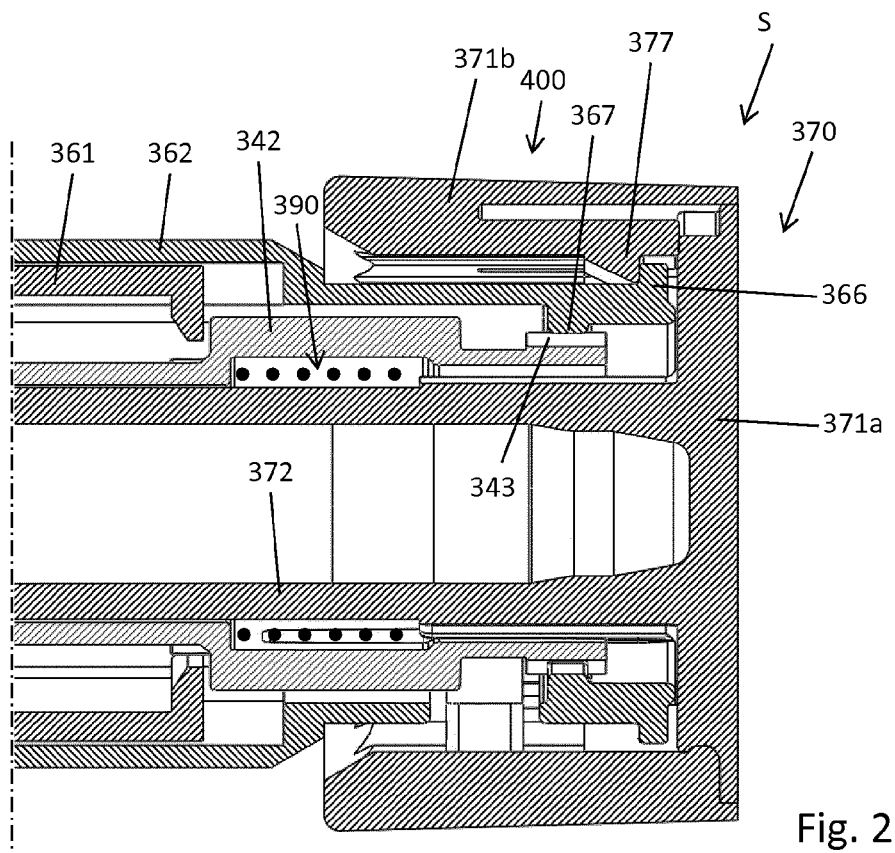
FIG. 29 is a longitudinal cross-section through the drive mechanism according to a further embodiment with the dose member in a proximal dose setting position.
Figure 30:
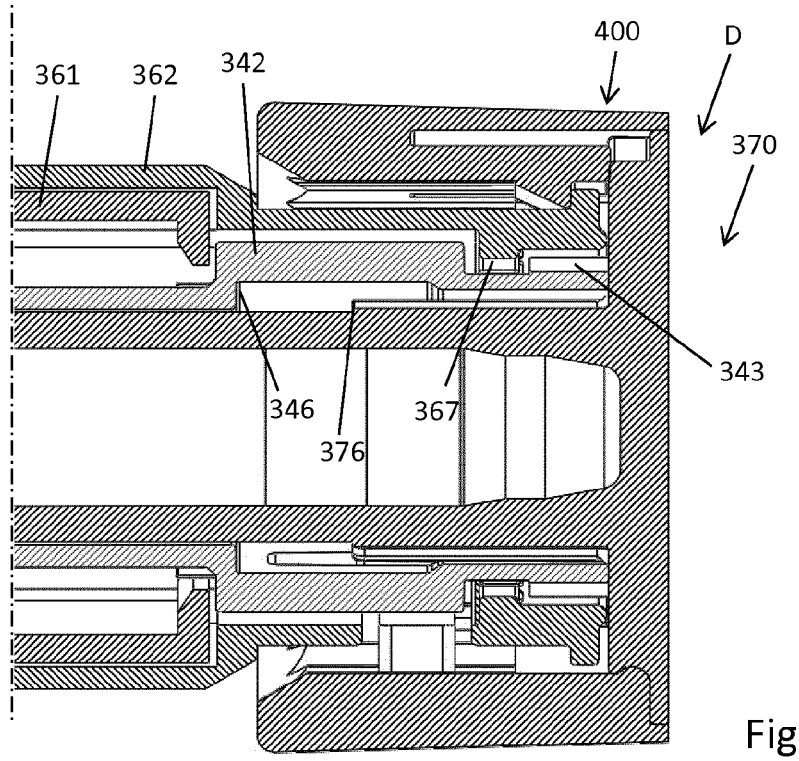
FIG. 30 is a longitudinal cross-section through the drive mechanism according to FIG. 29 but with the dose member in distal dose dispensing position.

As shown in FIG. 29 there is provided a spring 390 axially between the driver 340 and the dose member 370. In the present embodiment the driver 340 comprises a recessed portion along its inner circumference to receive the spring 390. A radially extending stepped portion 376 of the dose sleeve portion 372 of dose member 370 is axially engaged or axially coupled with the spring 390. In the present embodiment the spring 390 is configured as a compression spring that serves to displace the dose member 370 in proximal direction 5 relative to the driver 340. Consequently, the spring 390 axially sandwiched between a stepped portion 376 of the dose member 370 and a stepped portion 346 of the driver 340 is compressed as shown in FIG. 30 in comparison to the dose setting configuration as shown in FIG. 29. Due to the axial abutment of the dose member 370 with the blocking sleeve 362 the blocking sleeve 362 is also displaced in distal direction 4.

This leads to a disengagement of the mutually corresponding toothed structures 343 and 367. As a consequence the rotational engagement between the blocking sleeve 362 acting as a dial sleeve and the driver 340 is abrogated. As a dispensing position D has been reached the dose member 370, in particular its planar-shaped button part 371a comes into axial abutment with a proximal end face of the driver 340. A further depression of the dose member 370 in distal direction 4 then leads to a corresponding distally directed axial displacement of the driver 340. Since the driver is rotationally locked to the inner body 20 it is prevented from rotating during dose dispensing. The driver 340 is subject to a purely distally directed axial displacement so that the piston rod 300 is subject to a rotation due to the threaded engagement of the inner thread 342a with the piston rod thread 32.

The modified clutch 400, replacing the clutch C of FIG. 16 between the blocking sleeve 362 and the driver 340 is beneficial in that a separate blocking sleeve 172 as described in FIG. 15 is not required. So the embodiment of FIGS. 29-32 can be realized with at least one fewer component. In addition it is the blocking sleeve 362 that is subject to a small but distinct axial displacement when switching the drive mechanism 2 from the dose setting mode S into the dose dispensing mode D. The number sleeve 361 remains permanently threadedly engaged with the inner body 20 and is not subject to any axial sliding displacement during a switching of the drive mechanism between the dose setting mode and the dose dispensing mode.

LIST OF REFERENCE NUMBERS 1 injection device
2 drive mechanism
4 distal direction
5 proximal direction
10 housing
11 cartridge holder
12 outer body
13 layer
14 window
15 aperture
20 inner body
20a shaft
21 outer thread
22 spline
23 inner thread
24 stop
25 stop
30 piston rod
31 outer thread
32 outer thread
33 bearing
40 blocking structure
41 blocking segment
41b tangential end
42 blocking segment
42b tangential end
43 blocking segment
43b tangential end
44 blocking segment
44a tangential end
44 blocking segment
45a tangential end
46 gap
46a gap
47 blocking thread
48 distal edge
49 proximal edge
50 last dose nut
51 external rib
52 inner thread
53 stop
70 dose member
71 dose dial/dose button
73 arm
74 snap feature
80 cartridge
81 reservoir
82 bung
83 crimped metal cap
90 clutch sleeve
91 splines
92 teeth
93 aperture
94 splines
95 teeth
100 clicker
101 distal clicker
102 proximal clicker
103 clutch spring
104 splines
105 clicker teeth
106 clicker teeth
107 splines
108 splines
109 teeth
110 cartridge bias spring
120 cap
140 driver
141 distal drive sleeve
142 proximal drive sleeve
142a inner thread
142 inner thread
143 coupler
144 thread
145 stop
146 teeth
147 teeth
148 flexible finger
149 hook
160 display member
161 number sleeve
162 dial sleeve
163 inner thread
164 stop
165 clutch feature
166 bearing face
167 stop
168 clicker
170 dose member
171 dose button
171a button part
171b dial part
172 blocking sleeve
173 proximal end
174 blocking element
175 sidewall
176 fixing groove
177 protrusion
177a distal edge
177b proximal edge
178 base portion
179 groove
180 sidewall
181 aperture
182 locking tab
182a beveled edge
183 slit
184 recess
184 protrusion
186 recess
187 protrusion
188 recessed portion
189 stepped portion
190 pocket
191 extension
220 inner body
260 display member
261 blocking sleeve
262 dial sleeve
263 inner thread
264 recess
265 protrusion
273 proximal end
274 blocking element
275 sidewall
340 driver
341 distal drive sleeve
342 proximal drive sleeve
342a inner thread
343 toothed structure
346 stepped portion
360 display member 361 number sleeve
362 blocking sleeve
363 inner thread
364 recess
365 protrusion
366 rim
367 toothed structure
370 dose member
371 dose button
371a button part
371b dial part
372 dose sleeve portion
374 blocking element
375 sidewall
376 stepped portion
377 latch element
380 sidewall
381 aperture
390 spring
400 clutch

The invention claimed is:

1. A drive mechanism for an injection device for setting and dispensing of a dose of a medicament, the drive mechanism comprising:
an inner body fixable inside a housing of the injection device, the inner body comprising an elongated shaft extending in an axial direction, wherein the elongated shaft comprises an outer thread on an outer circumference of the elongated shaft and a blocking structure on the outer circumference of the elongated shaft;
a tubular-shaped display member having an inner thread engaged with the outer thread of the inner body;
a dose member axially displaceable between a dose setting position and a dose dispensing position relative to the inner body; and
a blocking sleeve permanently axially fixed to the dose member, rotationally fixed to the display member, and comprising at least one blocking element to axially engage with the blocking structure to block an axial displacement of the dose member from the dose setting position towards the dose dispensing position.

2. The drive mechanism according to claim 1, further comprising a torque transferring clutch between the dose member and the display member, wherein the clutch is configured to be closed when the dose member is in the dose setting position and wherein the clutch is disengageable by an axial displacement of the dose member relative to the display member.

3. The drive mechanism according to claim 2, wherein a distally directed displacement of the dose member relative to the display member is effectively impeded as long as the at least one blocking element is in axial engagement or axial abutment with the blocking structure.

4. The drive mechanism according to claim 1, wherein the blocking structure comprises a blocking thread axially extending on the elongated shaft of the inner body, wherein the blocking thread and the outer thread have the same pitch.

5. The drive mechanism according to claim 1, wherein the blocking structure comprises at least one spiral-shaped blocking segment and at least one gap or edge having a tangential size larger than or equal to a tangential size of the at least one blocking element.

6. The drive mechanism according to claim 1, wherein the blocking sleeve at least partially encloses the inner body and wherein the at least one blocking element protrudes radially inwardly from a sidewall of the blocking sleeve.

7. The drive mechanism according to claim 6 wherein the at least one blocking element extends radially inwardly through an aperture in a sidewall of the display member.

8. The drive mechanism according to claim 1, wherein the blocking sleeve encloses at least an axial section of the display member or a part of the display member.

9. The drive mechanism according to claim 1, wherein the dose member comprises a dose button with a button part and a dial part positively attachable and fixable to the button part to form an annular groove to axially engage with a proximal end section of the blocking sleeve.

10. The drive mechanism according to claim 1, wherein the display member comprises a dial sleeve and a number sleeve that are rotationally fixed to each other, wherein one of the dial sleeve and number sleeve is threadedly engaged with the inner body, and wherein the other one of the dial sleeve and number sleeve forms the blocking sleeve, comprises the at least one blocking element, and is engageable with the blocking structure.

11. The drive mechanism according to claim 10, wherein the dial sleeve is threadedly engaged with the inner body, and the number sleeve forms the blocking sleeve, comprises the at least one blocking element, and is engageable with the blocking structure, wherein the blocking structure is located at a distal section of the inner body, and wherein the at least one blocking element protrudes radially inwardly from a sidewall of the number sleeve.

12. The drive mechanism according to claim 10, wherein the outer thread is located at a proximal section of the inner body and wherein the inner thread is located on the dial sleeve.

13. The drive mechanism according to claim 1, further comprising a piston rod and a tubular-shaped driver extending in the axial direction, wherein the piston rod comprises a first outer thread engaged with an inner thread of the inner body and comprises a second outer thread of opposite hand engaged with an inner thread of the driver.

14. The drive mechanism according to claim 13, wherein the driver is rotationally locked to the dose member and wherein the driver is rotationally engageable with the display member via a clutch which is operable to:
rotationally engage the driver and the display member when the dose member is in the dose setting position and
further rotationally release the display member from the driver when the dose member is in the dose dispensing position.

15. The drive mechanism according to claim 13, wherein the dose member is axially fixed to the display member.

16. The drive mechanism according to claim 13, wherein the dose member is axially displaceable relative to the driver in an axial a distal direction against an action of a spring.

17. An injection device for setting and dispensing of a dose of a medicament, the injection device comprising:
a housing;
a drive mechanism comprising
an inner body fixable inside the housing, the inner body comprising an elongated shaft extending in an axial direction, wherein the elongated shaft comprises an outer thread on an outer circumference of the elongated shaft and a blocking structure on the outer circumference of the elongated shaft,
a tubular-shaped display member having an inner thread engaged with the outer thread of the inner body, a dose member axially displaceable between a dose setting position and a dose dispensing position relative to the inner body, and a blocking sleeve permanently axially fixed to the dose member, rotationally fixed to the display member, and comprising at least one blocking element to axially engage with the blocking structure to block an axial displacement of the dose member from the dose setting position towards the dose dispensing position; and a cartridge arranged inside the housing and filled with a liquid medicament.

18. The injection device of claim 17, further comprising a torque transferring clutch between the dose member and the display member, wherein the clutch is configured to be closed when the dose member is in the dose setting position and wherein the clutch is disengageable by an axial displacement of the dose member relative to the display member.

19. The injection device of claim 18, wherein a distally directed displacement of the dose member relative to the display member is effectively impeded as long as the at least one blocking element is in axial engagement or axial abutment with the blocking structure.

20. The injection device of claim 17, wherein the blocking structure comprises a blocking thread axially extending on the elongated shaft of the inner body, wherein the blocking thread and the outer thread have the same pitch.

* * * * *

UNITED STATES PATENT AND TRADEMARK OFFICE
CERTIFICATE OF CORRECTION

PATENT NO. : 10,881,806 B2
APPLICATION NO. : 16/061829
DATED : January 5, 2021
INVENTOR(S) : James Alexander Senior and Elliot Baxter Page 1 of 1

It is certified that error appears in the above-identified patent and that said Letters Patent is hereby corrected as shown below:

In the Claims

Column 36, Line 54, Claim 16, delete "an axial"

Signed and Sealed this
Twenty-third Day of March, 2021

Drew Hirshfeld
*Performing the Functions and Duties of the*
*Under Secretary of Commerce for Intellectual Property and*
*Director of the United States Patent and Trademark Office*